(12) United States Patent
Lee et al.

(10) Patent No.: US 10,174,332 B2
(45) Date of Patent: Jan. 8, 2019

(54) CONSTRUCTION OF NEW CUCUMBER FRUIT MOTTLE MOSAIC VIRUS DERIVED SUBGENOMIC PROMOTOR AND EXPRESSION VECTOR, AND USE THEREOF

(71) Applicant: CHUNG-ANG UNIVERSITY INDUSTRY-ACADEMIC COOPERATION FOUNDATION, Seoul (KR)

(72) Inventors: Gung Pyo Lee, Gyeonggi-do (KR); Sun Ju Rhee, Gangwon-do (KR)

(73) Assignee: CHUNG-ANG UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 112 days.

(21) Appl. No.: 15/303,174

(22) PCT Filed: Mar. 11, 2015

(86) PCT No.: PCT/KR2015/002358
§ 371 (c)(1),
(2) Date: Oct. 10, 2016

(87) PCT Pub. No.: WO2015/156506
PCT Pub. Date: Oct. 15, 2015

(65) Prior Publication Data
US 2017/0121725 A1    May 4, 2017

(30) Foreign Application Priority Data
Apr. 8, 2014  (KR) .................. 10-2014-0041785

(51) Int. Cl.
*C12N 15/82*    (2006.01)
*C12N 7/00*     (2006.01)
*C07K 14/005*   (2006.01)
*C12N 15/86*    (2006.01)

(52) U.S. Cl.
CPC ........ *C12N 15/8218* (2013.01); *C07K 14/005* (2013.01); *C12N 7/00* (2013.01); *C12N 15/8216* (2013.01); *C12N 15/86* (2013.01); *C12N 2770/00022* (2013.01); *C12N 2770/00043* (2013.01)

(58) Field of Classification Search
None
See application file for complete search history.

(56) References Cited

U.S. PATENT DOCUMENTS 8,344,208 B2 *  1/2013  Kearney ............ C12N 15/8203
                                           435/320.1

FOREIGN PATENT DOCUMENTS

KR    10-2012-0065906 A    6/2012
KR       10-1342084 B1    12/2013

OTHER PUBLICATIONS

Sequence Accession A2481200, Oct. 11, 2012, sequence alignment attached to office action.*
GenBank: JN226146.1, "Cucumber fruit mottle mosaic virus isolate Cm, complete genome", Dec. 10, 2011.
Lee, Geung Pyo(Chung AngUniversity), "Development of Cucurbit-Plant Specific Novel Virus Vector System", Formerly General Researcher Program Final(Result)Report, Ministry of Education and Science Technology, Jul. 30, 2013, pp. 4-10.
Lindbo, J.A., "High-efficiency protein expression in plants from agroinfectioncompatible Tobacco mosaic virus expression vectors", BMC Biotechnology, vol. 7, No. 52, Aug. 27, 2007, pp. 1-11.
Written Opinion for International Application No. PCT/KR2015/002358, dated Mar. 11, 2015 corresponding to Lee "Development of Cucurbit-Plant Specific Novel Virus Vector System", Formerly General Researcher Program Final (Result)Report, Ministry of Education and Science Technology, Jul. 30, 2013, pp. 4-10. [Both Documents Attached].

* cited by examiner

*Primary Examiner* — Elizabeth F McElwain
(74) *Attorney, Agent, or Firm* — Riverside Law LLP

(57) ABSTRACT

The purpose of the present invention is to develop a cucumber fruit mottle mosaic virus vector so as to enable a study of gene function through gene silencing phenomenon in Cucurbitaceae plants, which has been difficult to study in the past, and to enable the study in fruits as well through stable expression. Furthermore, the present invention establishes a system that enables expression of a heterologous protein in plants, thereby, for the first time, providing a vector applicable to both the gene silencing phenomenon and protein expression in Cucurbtaceae plants.

20 Claims, 14 Drawing Sheets
Specification includes a Sequence Listing.

| Primer | Sequence | |
|---|---|---|
| SJ 413 | 5'- GGAGGAGGGAACAACAAGAGG-3' | Nb-GADPH-F |
| SJ 314 | 5'- AGATGCCGTCAGTGCCGA-3' | Nb-GADPH-R |
| SJ 565 | 5'-CGCTTTGATTTTCCTGAAGCA-3' | NbPDS-F |
| SJ 566 | 5'- GCTGGCAAGAGTCCAATAGC-3' | NbPDS-R |
| SJ 415 | 5'- GGCGGATGTTGCTTTAAGGA-3' | Cm-18S-F |
| SJ 416 | 5'-GTGGTGCCCTTCCGTCAAT-3' | Cm-18S-R |
| SJ 561 | 5'-TGCATTTTGATTGCCTTGAA-3 | CmPDS-F |
| SJ 562 | 5'- TATGCTCGACAATTGGCTCA-3' | CmPDS-R |
| SJ 571 | 5'- AGAACGGCATCAAGGTGAACT-3' | EGFP-F |
| SJ 572 | 5'- TGCTCAGGTAGTGGTTGTCG-3' | EGFP-R |

FIG. 13
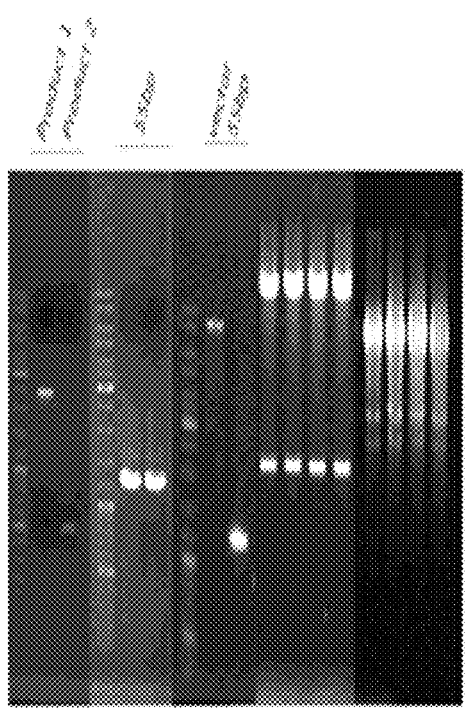
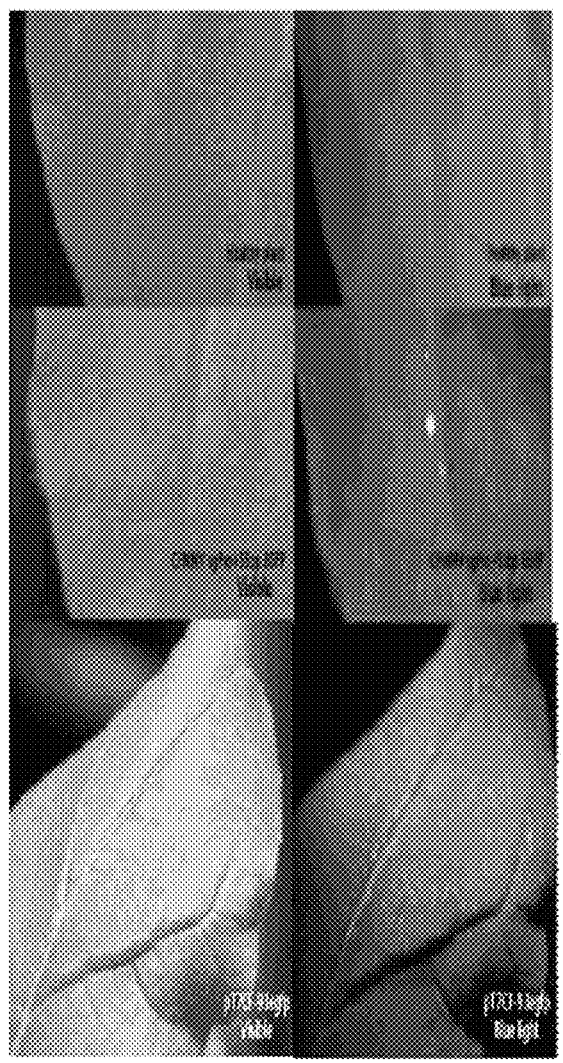

CONSTRUCTION OF NEW CUCUMBER FRUIT MOTTLE MOSAIC VIRUS DERIVED SUBGENOMIC PROMOTOR AND EXPRESSION VECTOR, AND USE THEREOF

CROSS-REFERENCE TO RELATED APPLICATIONS

This application is the U.S. national phase application filed under 35 U.S.C. § 371 claiming benefit to International Patent Application No. PCT/KR2015/002358, filed on Mar. 11, 2015, which is entitled to priority under to Korea application no. 10-2014-0041785, filed Apr. 8, 2014.

The present invention was undertaken with the support of Supporting System Development of Molecular Breeding for Watermelon Seeds Export using Pathogen Resistance and Chromosomal Variants No. 213002041SBR10 grant funded by the Ministry of Agriculture, Food and Rural Affairs (MAFRA).

TECHNICAL FIELD

The present invention relates to a new Cucumber fruit mottle mosaic virus (CFMMV)-derived subgenomic promoter (SGP) and a CFMMV vector including the promoter.

The present invention also relates to a composition which includes the vector for plant transformation, a host plant transfected by the vector, and a method of inducing gene silencing or gene expression in plants using the vector.

BACKGROUND ART

Today, an analysis of the nucleotide sequence of a plant is rapid due to advancing sequencing methods and cost reduction. Among Cucurbitaceae plants, recently, full-length sequences of cucumber (2009), melon (2012), and watermelon (2013) were disclosed, but, in construction of a transformant, there is a difficulty in conducting a study on gene function through reverse or forward genetics due to a low success rate and inadequate development of a tool for a gene function analysis. To solve such a problem, viral vectors that can be studied are being developed. While viral vectors capable of being applied to other crops such as tomatoes, peppers, beans, etc. have been developed over time, the only choice for Cucurbitaceae plants is Apple latent stunt virus, which was developed in Japan in 2009. A vector constructed to express a heterologous protein in plants based on *Tobamovirus*, which infects cucurbits, is the Cucumber green mottle mosaic virus (CGMMV), which had an expression result without a prediction of a subgenomic RNA promoter (SGP) with a small-sized epitope attached behind the coat protein. Therefore, to achieve gene silencing and stable heterologous protein expression, an attempt was made to construct a vector by isolating and identifying CFMMV using Cucurbitaceae plants as main hosts. CFMMV is a member of the genus *Tobamovirus*, for which crops such as Cucurbitaceae plants including cucumbers, pumpkins, melons, oriental melons, watermelons, gourds, and tobacco plants are hosts.

The inventors submitted the full-length sequence of CFMMV that had been previously isolated and identified to the NCBI Genbank (Accession no. JN226146) and also received a patent for a recombinant clone of a CFMMV-derived attenuative virus (10-1342084). The present invention is for expressing the whole or a part of an insert in a host plant by inserting an innate gene of the host plant through artificial modification of the nucleotide sequence of CFMMV or inserting a gene of a foreign organism.

*Tobamovirus* is characterized by having a single genome, whose subgroups include Solanaceae-, Cruciferae- and Cucurbitaceae-infectious *Tobamoviruses*, and recently, Malvaceare-infectious and Cucurbitaceae-infectious *Tobamoviruses* have been reported. Development and research on viral vectors using tobacco mosaic virus (TMV), which is a representative *Tobamovirus*, and tomato mosaic virus (ToMV), tobacco mottle green mosaic virus (TMGMV) and sunn-hemp mosaic virus (SHMV) have been successfully performed in tobacco and tomato.

In the development of viral vectors, it is important to select an insertion position of a multiple cloning site (MCS), and, following the position selection, subgenomic promoter (SGP) mapping should be preferentially performed.

The inventors intend to provide a host plant-infectious viral vector that can be used in studying a gene function through gene silencing in Cucurbitaceae plants, which is difficult, and can also in vivo express a heterologous protein in plants.

DISCLOSURE

Technical Problem

An aspect of the present invention is to provide a new CFMMV-derived subgenomic promoter (SGP).

Another aspect of the present invention is to provide a CFMMV vector including the promoter.

Still another aspect of the present invention is to provide a host plant transfected by a vector, and a transformed cell line.

Yet another aspect of the present invention is to provide a composition including the vector or cell line for transformation and a method of inducing gene silencing or gene expression in plants using the same.

Technical Solution

An aspect of the present invention provides a subgenomic promoter (SGP) consisting of a nucleotide sequence from −204 bp to +160 bp from the start codon of the coat protein of CFMMV.

In the present invention, the CFMMV is a member of the *Tobamovirus*, which is, like other *Tobamoviruses*, a positive sense-single stranded (ss) RNA virus whose genetic information exists on RNA. The CFMMV genome consists of a nucleotide sequence of SEQ. ID. NO: 1.

The term "promoter" used herein refers to a DNA sequence capable of regulating expression of a coding sequence or functional RNA. In the present invention, the promoter consists of a nucleotide sequence from −204 bp to +160 bp from the start codon of the coat protein, and the start codon of the coat protein of the CFMMV may be located at nucleotides 5855 to 5857 of the CFMMV genome of SEQ. ID. NO: 1.

Also, the subgenomic promoter may consist of a nucleotide sequence from one selected from the group consisting of −204 bp, −187 bp, −180 bp, −170 bp, −163 bp, −157 bp, −152 bp, −148 bp, −143 bp, −135 bp, −127 bp, −121 bp, −110 bp, −100 bp, −93 bp, −81 bp, −77 bp, −55 bp and −30 bp to +160 bp from the start codon of the coat protein and, most preferably, consists of a nucleotide sequence from −93 bp to +100 bp from the start codon of the coat protein. The subgenomic promoter consisting of the nucleotide sequence from −93 bp to +100 bp from the start codon of the coat protein may be represented by a nucleotide sequence of SEQ. ID. NO: 2.

In one embodiment of the present invention, CFMMV is derived from a dry melon leaf provided from a Virus GenBank. The CFMMV was subjected to full-length cloning to ensure an infectious full-length clone, and based on the clone, construction of gene-insertable MCS was attempted.

In one embodiment of the present invention, the secondary structure of subgenomic RNA of CFMMV was predicted in order to find the range of SGP for coat protein expression, and the SGP range showing the highest efficiency was provided through promoter mapping.

Also, one aspect of the present invention provides a CFMMV vector including the subgenomic promoter.

The term "vector" used herein indicates serving to induce gene silencing in host plants or to deliver a nucleotide fragment for inducing gene expression to a host plant, and the vector of the present invention includes a CFMMV-derived subgenomic promoter.

In the vector of the present invention, a nucleotide sequence for inducing gene silencing or gene expression is operably linked to the CFMMV-derived subgenomic promoter. The term "operably linked" used herein refers to a functional linkage between a nucleic acid expression regulatory sequence (i.e., promoter sequence) and a different nucleic acid sequence, and thus the regulatory sequence regulates transcription and/or translation of the different nucleic acid sequence.

In addition, the vector of the present invention includes at least one restriction enzyme recognizing nucleotide sequence capable of cloning a nucleotide sequence encoding a protein for expression, that is, a multiple cloning site (MCS) sequence. Restriction enzymes include, for example, Eag I, EcoR I, EcoR II, BamH I, Bgl II, BstB I, Hind III, Taq I, Not I, Hinf I, Sau3A, Pac I, Pov II, Sma I, Hae III, Hga I, Alu I, EcoR V, EcoP15 I, Kpn I, Pst I, Sac I, Sal I, Sca I, Spe I, Sph I, Stu I, Xba I, and Xho I, but the present invention is not limited thereto.

Also, the vector of the present invention may be additionally fused with a different sequence to facilitate purification of a recombinant target protein expressed from the vector, and the additional sequence may be, for example, a sequence encoding glutathione S-transferase (GST), maltose-binding protein (MBP), FLAG, 6× hexahistidine (His), N utilization substance A (NusA) or thioredoxin (Trx). Due to the additional sequence for purification, the protein expressed in a host may be rapidly and easily purified by affinity chromatography.

Also, the nucleotide sequence for inducing gene silencing in the vector of the present invention may be RNA interference (RNAi), small interference RNA (siRNA), short hairpin RNA (shRNA), and micro RNA (miRNA), etc.

Also, the vector of the present invention may further include a CFMMV T7 (SEQ. ID. NO: 5) or SP6 (SEQ. ID. NO: 6) promoter, or a CaMV 35S promoter.

The CFMMV vector according to the present invention may effectively induce gene silencing or gene expression in host plants. It can be applied to study gene silencing and in vivo expression of a heterologous protein and particularly may be more effectively utilized in Cucurbitaceae plants.

Another aspect of the present invention provides a cell line transformed by the vector.

The cell line is not limited in type, and encompasses all cell lines which can infect plants. In an embodiment of the present invention, *Agrobacterium* was used.

Still another aspect of the present invention provides a host plant transfected by the vector or cell line.

The host plant may be a Cucurbitaceae plant. Examples of the non-limiting Cucurbitaceae plants may include pumpkin, cucumber, watermelon, melon, oriental melon, gourd, and sponge gourd.

Yet another aspect of the present invention provides a composition including the CFMMV vector or the cell line for plant transformation.

The composition may further include a P19 suppressor. The P19 suppressor may be RNA interference (RNAi), a small interference RNA (siRNA), short hairpin RNA (shRNA), or micro RNA (miRNA), but the present invention is not limited thereto.

The term "transformation" used herein refers to conversion of the phenotype of a host by injecting foreign DNA into host cells, and throughout the specification, the transformation is substituted with various terms such as transfection, transformation, and transduction.

Yet another aspect of the present invention provides a method of inducing gene silencing or gene expression in plants, the method including inoculating a plant with the CFMMV vector or the cell line.

The method may include further inoculating the plant with a P19 suppressor.

In an embodiment of the present invention, a CFMMV vector (p35sCF.001) including a CaMV 35S promoter, which facilitates transcription in plants, is provided. A vector for proliferating CFMMV was developed by inserting the same vector into an expression vector for transformation using a transcription mechanism in plants.

In an embodiment of the present invention, a method of infecting p35sCF.001 with high efficiency is provided. When GV3101-pPM90 in the *Agrobacterium* family is transformed with p35sCF.001 and then the resulting transformant is injected into plant leaves, inoculation efficiency reaches approximately 100%. Also, the action of viral proliferation suppressing mechanism (defense mechanism) of plants in expression of a heterologous protein significantly reduces an expression level. Therefore, the present invention includes improving expression of a heterologous protein and virus proliferation even in CFMMV by co-inoculation of p35sCF.001 with the P19 protein which was previously reported.

In addition, in one embodiment of the present invention, a method of inserting an insert having the highest efficiency when applied in gene silencing is provided. Because of the characteristics of the vector provided from the present invention, for gene silencing, only approximately 200 to 300 bp of a fragment is inserted, rather than a whole target gene. In this case, efficiency varies according to a gene position and a method. When two adjacent fragments with the 5'-terminus and the 3'-terminus attached at both ends were inserted into a viral vector, the highest gene silencing efficiency was shown. In watermelon, a viral vector was stably retained until it grows up to get fruit, and gene silencing was also shown.

Advantageous Effects

The CFMMV vector according to the present invention may effectively induce gene silencing or gene expression in host plants. It can be applied to study the gene silencing and in vivo expression of a heterologous protein and particularly may be more effectively used in Cucurbitaceae plants.

DESCRIPTION OF DRAWINGS

FIG. 3 shows a prediction of the secondary structure of RNA for SGP mapping for a region upstream from the start codon of a coat protein and a schematic diagram of a variant vector.

Figure 5:
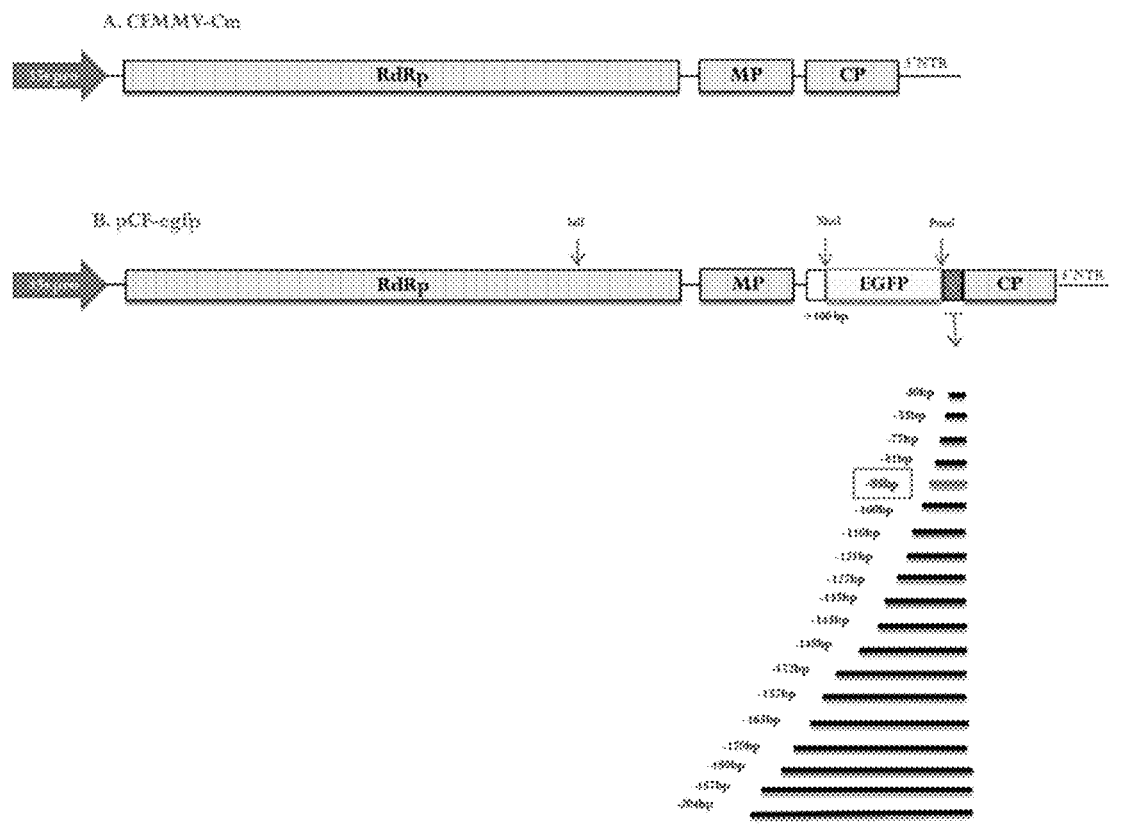

FIG. 5 is a schematic diagram completed by being constructed based on SGP mapping of a coat protein.

FIG. 11 is a list of primers used in Real-time qPCR.

FIG. 13 is an electrophoresis image of a product obtained by cloning of a CFMMV vector including a T7 promoter and in vitro transcription, and a result of egfp expression in inoculated leaves of *N. benthamiana* when inoculated with the product.

MODES OF THE INVENTION

Hereinafter, the present invention will be described in further detail. Examples are merely provided to more fully explain the present invention, and it is obvious to those of ordinary skill in the art that, according to the gist of the present invention, the scope of the present invention is not limited to these examples.

<Example 1> Construction of CFMMV Vector

For gene insertion, MCS constructs which do not exist in viruses proliferated in the nature are required. Also, promoters capable of expressing a gene inserted into MCS are needed, and SGP is used, considering the features of the viruses. Since the SGP range of Cucurbitaceae-infectious *Tobamovirus* including CFMMV has not been studied, it will be provided in the present invention.

Figure 1A:
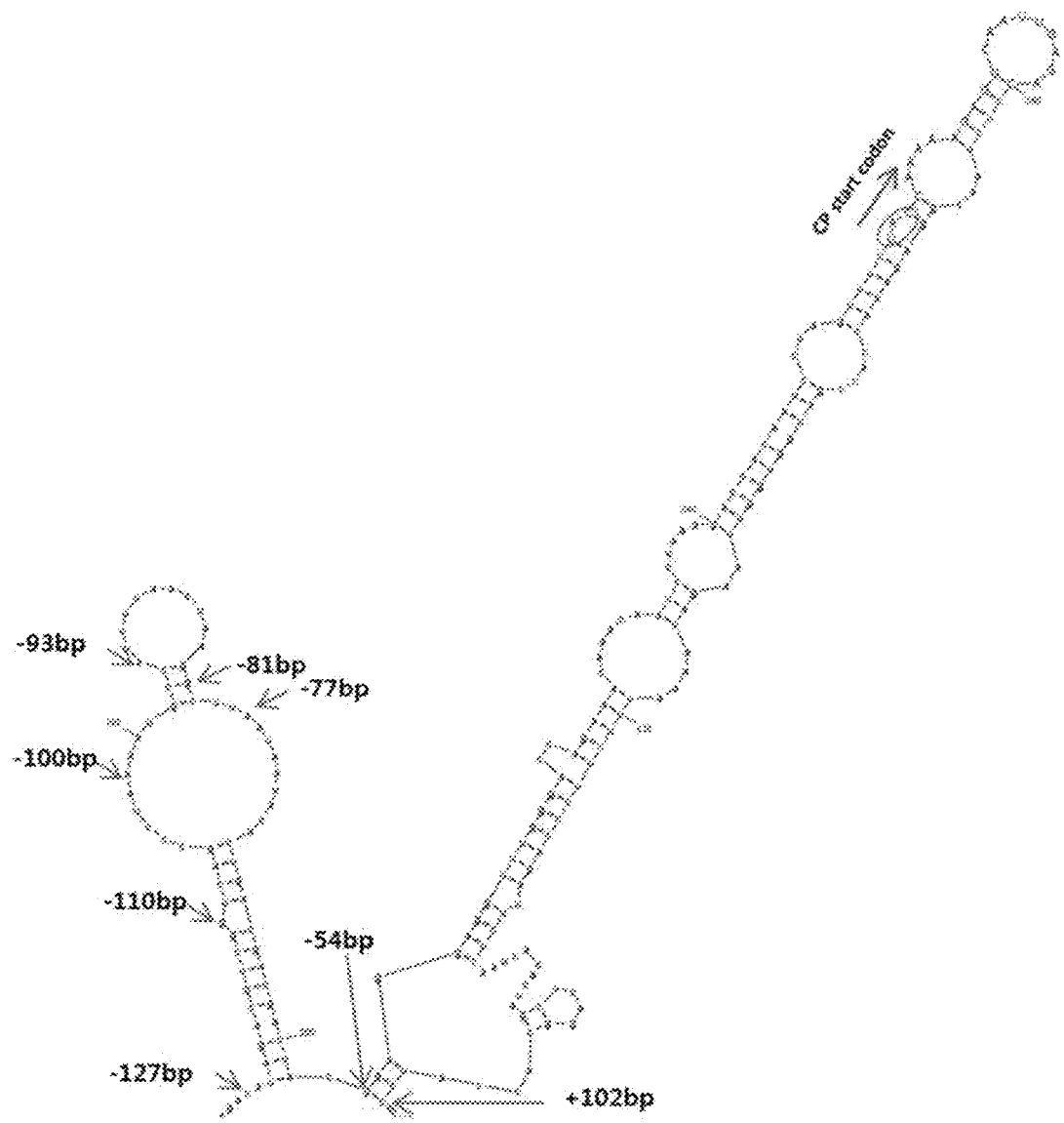
FIG. 1 shows a prediction of the secondary structure of RNA for SGP mapping of a region downstream from the start codon of a coat protein and a schematic diagram of a variant vector.

<Example 1-1> Prediction of Two-Dimensional Structure of SGP of CFMMV Coat Protein A promoter-specific structure was identified using an RNA prediction program to utilize SGP of the coat protein, and then several estimated ranges were selected. An antisense RNA sequence from MP to CP was inserted into an Mfold web server program, and an RNA secondary structure at the lowest energy level was constructed (FIG. 1a).

<Example 1-2> Promoter Mapping from CFMMV Clones (Mapping of Downstream Region of Start Codon)

Figure 1B:
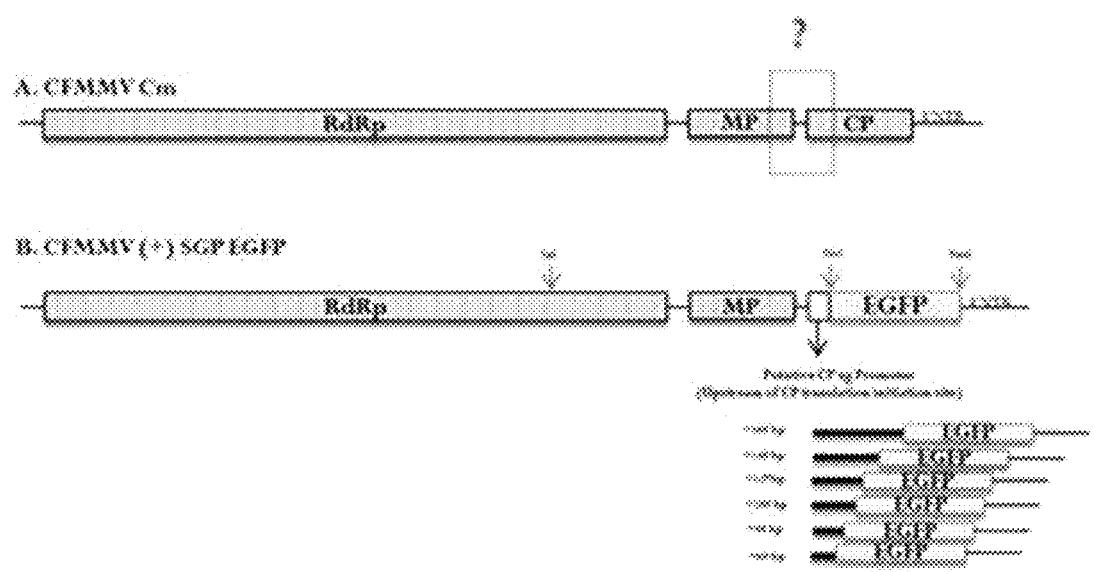

SGP exists upstream and downstream with respect to the start codon (ATG) of the coat protein. To find the range of an operated promoter, the coat protein was substituted with enhanced green fluorescence protein (EGFP) which is able to facilitate visual detection of protein expression, and each of vectors including the range of +68, +88, +100, +127, +140 and +160 bp from the start codon of the coat protein was cloned (FIG. 1b). Here, the start codon of the coat protein in changed from ATG to ACG. The resulting viral vector was transfected into *Agrobacterium*, which was injected into *N. benthamiana* to observe EGFP expression in the inoculated leaves. It was confirmed under blue light that subjects inoculated with CFMMV vectors with +100 bp at 6 dpi showed the highest protein expression. Six leaf discs were equally harvested from the agroinfected ranges of inoculated leaves to extract proteins. Equivalent amounts of the proteins were analyzed by electrophoresis and western blotting, and the results thereof are shown in FIG. 2.

Figure 2:
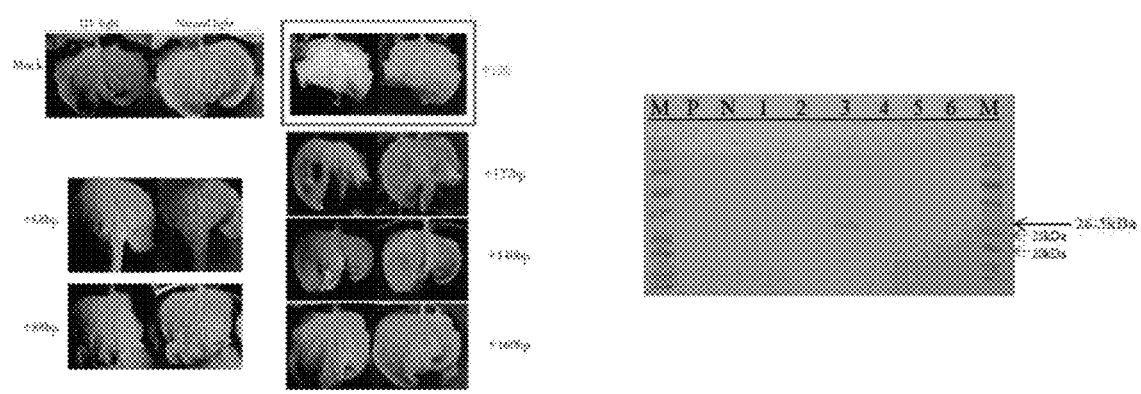
FIG. 2 shows EGFP gene expression according to the mapping of a region downstream from the start codon of a coat protein. A vector having +100 bp of SGP showed high EGFP expression under blue light, which was also shown by Western blotting. Lane M-protein marker; Lane P—positive control (CFMMV-Cm, *N. benthamiana*); Lane N—negative control (Mock); Lane 1—pCF(+)68 bp-egfp; Lane 2—pCF(+)88 bp-egfp; Lane 3—2pCF(+)100 bp-egfp; Lane 4—pCF(+)127 bp-egfp; Lane 5—pCF(+)140 bp-egfp; Lane 6—pCF(+)160 bp-egfp.

As shown in FIG. 2, EGFP protein expression was detected only from +100 bp inoculated subject.

<Example 1-3> Upstream Mapping of Start Codon of CFMMV Coat Protein

Figure 3:
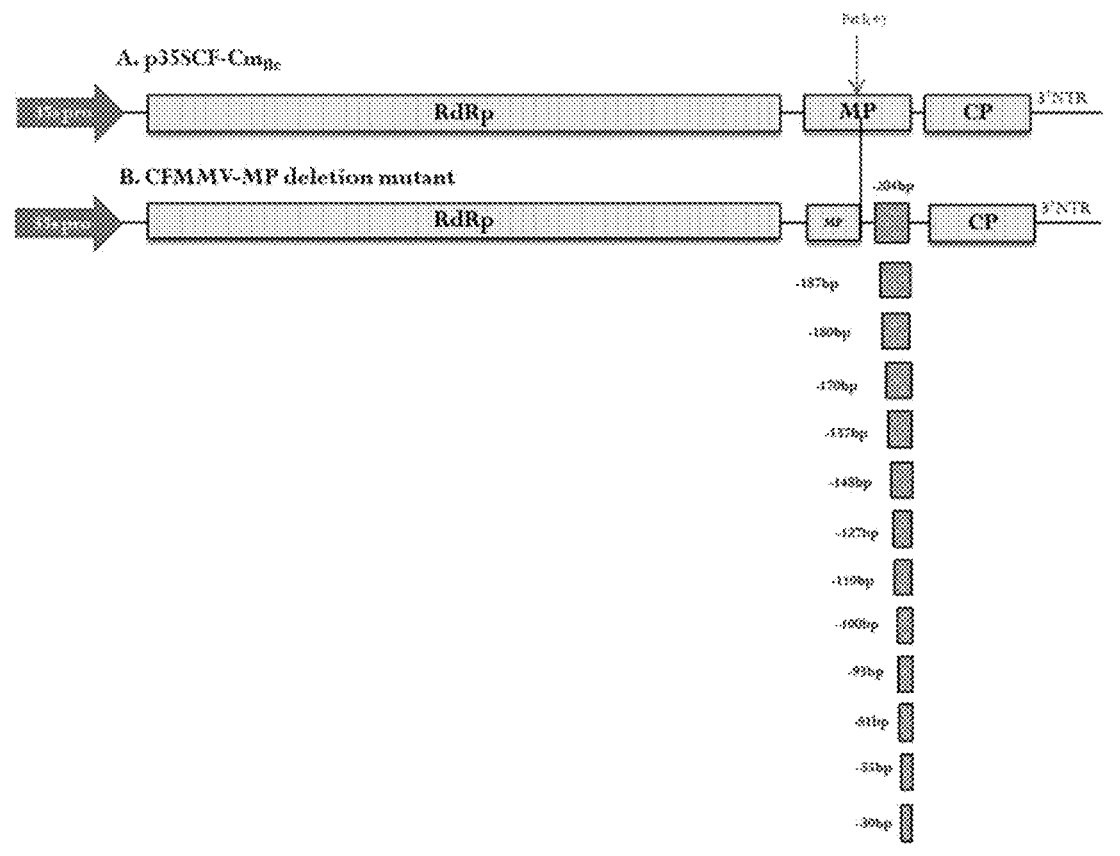

To determine the downstream promoter range from the start codon, a part of the downstream of the start codon of the coat protein was removed (movement protein-encoded region), and the expression of the coat protein was identified. 13 mutants from −204 to −30 bp upstream the start codon of the coat protein were constructed (ΔMP-30 bp~204 bp, FIG. 3), and each was injected into leaves of *N. benthamiana*. Six leaf discs were equally harvested from the agroinfected regions of the inoculated leaves so as to extract proteins, which were identified through SDS-PAGE. The results are shown in FIG. 4.

Figure 4:
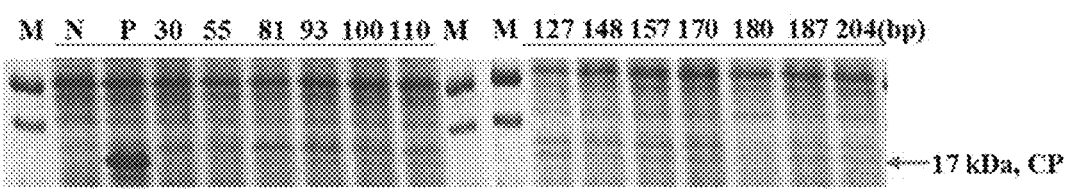
FIG. 4 shows the expression of a coat protein confirmed by SDS-polyacrylamide gel electrophoresis by inoculating *N. benthamiana* with clones constructed by SGP mapping of a region upstream from the start codon of the coat protein and extracting a protein from the inoculated leaf thereof. It was confirmed that coat protein expression occurred in all samples except ΔMP-30 bp. Lane P—positive control (CFMMV-Cm, *N. benthamiana*); Lane N—negative control (Mock); Lane 30~204 bp (ΔMP-30 bp~204 bp variant clone).

As shown in FIG. 4, expression of all proteins except ΔMP-30 bp was identified.

<Example 2> Construction of CFMMV Vector Through the Most Efficient SGP Selection Based on the mapping results, while downstream +100 bp was fixed, vectors having 19 different (−30 bp, −55 bp, −77 bp, −81 bp, −93 bp, −100 bp, −110 bp, −121 bp, −127 bp, −135 bp, −143 bp, −148 bp, −152 bp, −157 bp, −163 bp, −170 bp, −180 bp, −187 bp, −204 bp) SGPs were constructed and injected into *N. benthamiana*, followed by selection of a vector having SGP showing the highest efficiency. As a result, the highest EGFP expression was shown from the vector having SGP from −93 bp to +100 bp (pCF93-egfp).

<Example 3> Sequencing for Selected CFMMV Vector

A nucleotide sequence of the selected vector pCF93-egfp was analyzed by SolGent, and the result is set forth in SEQ. ID. NO: 3.

<Example 4>*Agrobacterium* Transformant for CFMMV Vector Inoculation and Inoculation Among inoculation methods with a CFMMV vector having a 35S promoter, the most effective method is agroinfection. 50 ng of the vector was transformed to *Agrobacterium*-family GV3101 (or GV3101-pPM90) by an electric shock, and the resultant cells were grown in a 5-ml tube containing LB medium by shaking the culture at 28° C. for approximately 16 hours and then subcultured in 30 ml LB medium. Here, 0.01 M MES (pH 5.6) and 20 μM acetosyringone were added to 30 ml LB medium and cultured with shaking at 28° C. up to $O.D_{600}$=0.8~1.0, followed by collecting the cells by centrifugation at 6000 rpm for 5 minutes. Inoculants (4.4 g/L of MS salt, 0.01M MES (pH 5.6), 2% sucrose, 200 μM acetosyringone) were added and diluted to activate viruses at room temperature over 4 hours. The activated viruses were injected into the backside of leaves using 1 ml syringe without a needle.

<Example 5> RNA and Protein Extraction

Following grinding the harvested sample in liquid nitrogen, 800 μl reagent (MRC) prepared by adding 8 μl mercaptoethanol to the powder was added and stirred at 65° C. for 5 minutes. The resulting product was centrifuged at 13000 rpm for 3 minutes to obtain a supernatant, which was transferred to a new tube, treated with 300 μl chloroform, and vortexed for 15 seconds. The resultant product was centrifuged at 13000 rpm and 4° C. for 15 seconds, and then a supernatant was transferred to a new tube. An equivalent amount of isopropanol was added to the tube and precipitated at −20° C. for 20 minutes. A washing procedure, which includes centrifugation of the pellets at 13000 rpm and 4° C. for 10 minutes, discarding of isopropanol, addition of 1 ml of 70% ethanol, and then centrifugation of the resulting solution at 13000 rpm and 4° C. for 10 minutes, was performed twice. After remaining ethanol was completely removed, the pellets were dissolved in 30 μl water and treated with DNase I, thereby isolating only pure RNA.

Leaf samples were ground in liquid nitrogen. 900 μl of RNA extraction buffer was added to a 2 ml tube and stirred well, followed by addition of 900 μl phenol and gentle vortexing. The resulting product was centrifuged at 13000 rpm and 4° C. for 15 minutes to recover an intermediate protein layer. The above procedure was purified through PCI treatment twice to recover a protein. The protein was precipitated in 100% acetone at −20° C. for approximately 1 hour and isolated by centrifugation at 10000 g and 4° C. for 10 minutes, followed by completely discarding acetone and then washing with 80% acetone several times. The recovered protein was naturally dried for approximately 30 minutes and then dissolved in 100 μl of 1% SDS.

<Example 6> Real-Time qPCR for Confirming CFMMV Vector Efficiency

From *N. benthamiana* infected by a vector having −81 bp, −100 bp or −110 bp of SGP with respect to −93 bp, which showed the highest expression of a green fluorescent protein as visually detected, RNAs of inoculated upper second leaves were extracted, and in order to synthesize cDNA from isolated and purified RNA, RT-PCR was performed with 20 μl of a reaction mixture including 2 μg of total RNA, 1× buffer, 10 mM dNTP, 0.05M DTT, 40 U RNase Inhibitor, and 200 U Superscript III reverse transcriptase using 100 ng of a random hexamer. For comparative quantification using cDNA 1/10 diluent as a template, a primer for GAPDH gene was constructed to be used in normalization between samples. To quantify a target gene, EGFP-specific primers were used, and the primers are shown in FIG. 11.

Figure 6:
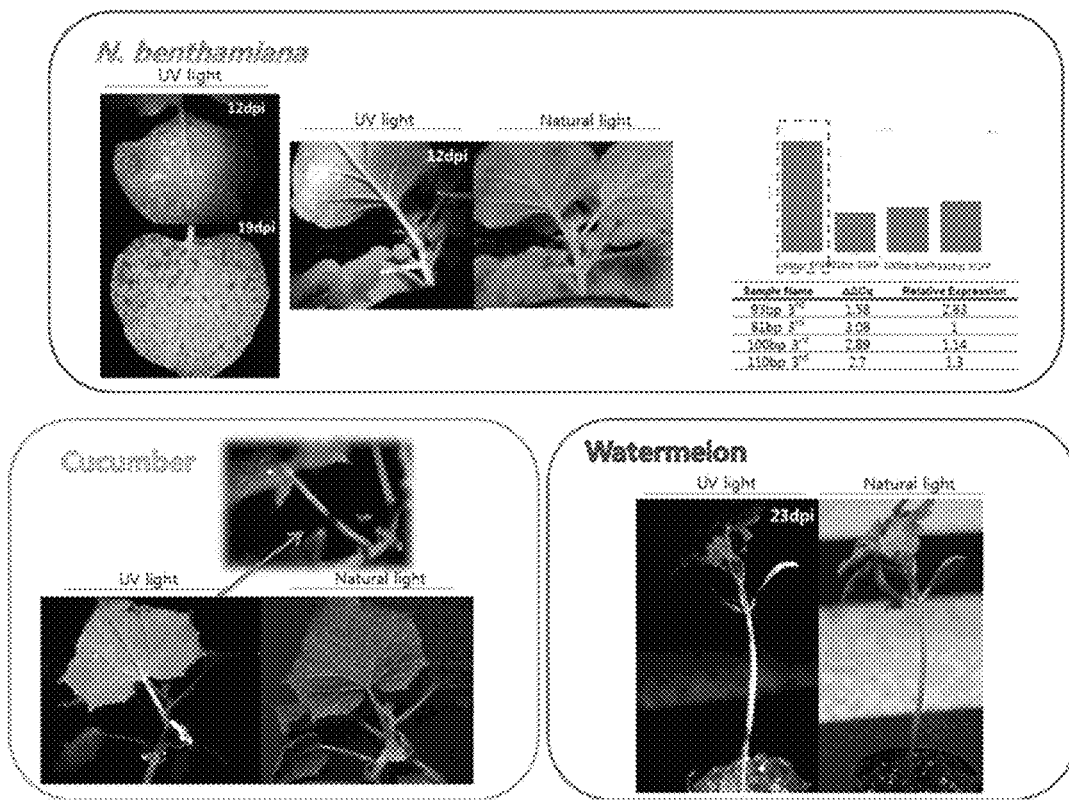
FIG. 6 shows EGFP expression confirmed by inoculating *N. benthamiana* with a vector having SGP from -93 bp to +100 bp and relative quantification of EGFP expression levels through real-time qPCR by extracting RNA of upper two leaves of *N. benthamiana* infected by the vector having -81, -100 or -110 bp of SGP with respect to -93 bp. It was confirmed that a pCF93-egfp-inoculated subject exhibited the highest mRNA expression level of EGFP.

Real-time qPCR was performed using a final 20 μl reaction mixture including the following substances: 2 μl of the first chain cDNAs, 2× master mix, and 20× Evagreen dye (Biofact Co.). PCR was performed under the following temperature conditions: 40 cycles of 94° C. for 12 minutes, 94° C. for 10 seconds, and 60° C. for 30 seconds. According to the PCR results, it was confirmed that the 35SCF-93 bp::EGFP inoculated subject maintains the highest expression level of EGFP mRNA (FIG. 6).

Figure 7:
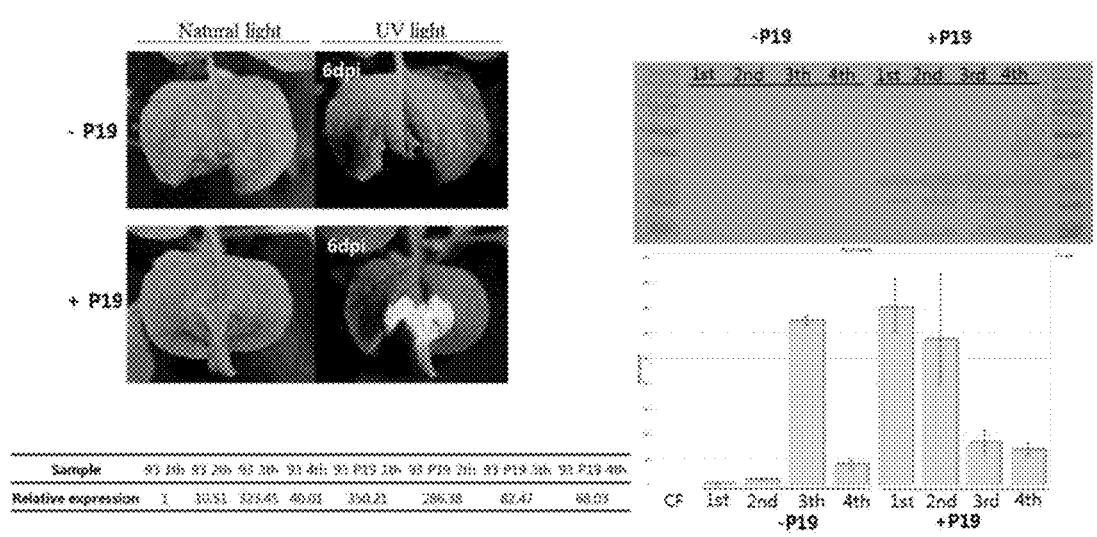
FIG. 7 shows comparative expression levels of green fluorescent proteins according to co-inoculation with P19. RNAs of whole inoculated leaves, inoculated upper second, third, and fourth leaves of *N. benthamiana* were extracted to confirm the difference in mRNA expression levels of EGFP through real-time qPCR, and proteins were extracted to confirm the difference in EGFP protein expression through western blotting.

<Example 7> Comparison of Expression Levels of Heterologous Protein in Co-Inoculation with P19 Suppressor In single-inoculation with pCF93-egfp vector and co-inoculation with a P19 suppressor and a vector, EGFP expression levels in inoculated leaves and upper leaves were determined on RNA and protein levels. The P19 suppressor serves to suppress post-transcriptional gene silencing (PTGS) and particularly serves to maintain virus proliferation without damage by preventing degradation of a dsRNA-type viral product formed in a virus proliferation process by a plant preventive mechanism. Therefore, in this study, the P19 suppressor was used to maintain the high expression level of EGFP mRNA included in the virus, as well as the virus, and thus increase the expression level of a heterologous protein in plants. Co-inoculation was performed by transforming a vector including a 35S promoter and a P19 gene into *Agrobacterium* GV3101 and injecting a mixture of the resulting inoculant and pCF93-egfp at a ratio of 1:1. From inoculated leaves (1st) and inoculated upper second (2nd), third (3rd) and fourth (4th) leaves, six leaf discs were harvested to extract both RNA and proteins according to the method described in Example 5, and protein expression levels were visualized by western blotting (disclosed in Example 8). Also, as disclosed in Example 6, cDNA was synthesized and analyzed under the same condition and composition through real-time quantitative PCR to compare mRNA expression levels of egfp. In the single-inoculation with a vector, when a fluorescence value of the egfp expression level of the inoculated leaves was set as 1 to digitize a relative quantification value, the sum of expression levels from four leaves was 374.97, and the sum of expression levels from four leaves when co-inoculated with a P19 suppressor was 787.09. In the co-inoculation with the P19 suppressor, an approximately two-fold increase in egfp mRNA was shown (FIG. 7).

<Example 8> SDS-PAGE and Western Blotting for Confirming Green Fluorescent Gene Expression A protein sample was isolated from an SDS-polyacrylamide gel, and a nitrocellulose (NC) membrane was transferred by electroblotting using an electrotransfer apparatus (Bio-Rad, USA). A blotted membrane was carefully separated and transferred to an SNAP-id system (Millipore Co.) to bind antibodies to proteins on the membrane according to the sequence of blocking, $1^{st}$ antibody (1:1000 GFP, Clontech Co.) binding, washing, $2^{nd}$ antibody (1:7500; Anti-Rabbit IgG Ap conjugate, Promega Co.) binding, and washing. The membrane on which the binding was completed was reacted with an alkaline phosphatase (AP) solution (100 mM Tris-Cl, pH8.0; 100 mM NaCl, 5 mM $MgCl_2$) for 1 minute, and 1 mL of Western Blue stabilized substrates (Promega Co.) with respect to the alkaline phosphatase was added.

<Example 9> Gene Silencing Using CFMMV Vector

Gene silencing was observed in Cucurbitaceae plants by inserting a part of a target gene into vectors having SGP of the coat protein, which were different from the selected vector.

<Example 9-1> Cloning and Insertion of Target Gene

Figure 8:
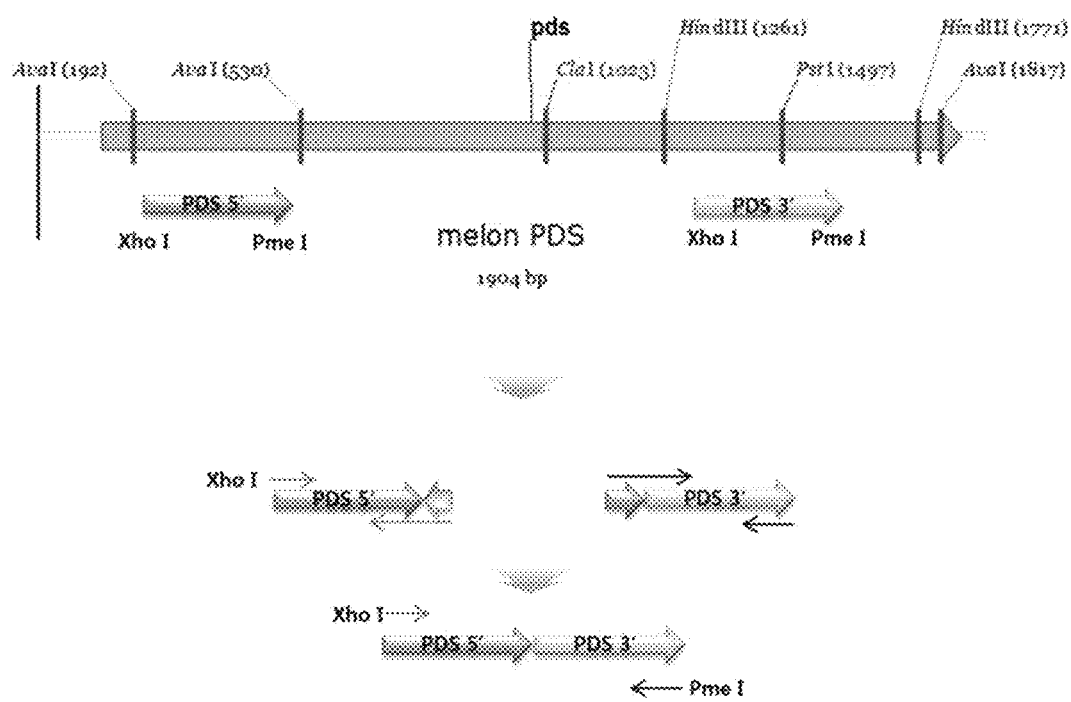
FIG. 8 is a schematic diagram illustrating a position of inserted pds gene and a cloning method.

As a target gene, a Phytoene desaturase (pds) gene, which forms a β-carotene synthesis pathway, was selected. cDNA was synthesized from 2 μg of RNA extracted from each plant using superscript III reverse transcriptase and oligo dT primers and cleaved with XhoI-PmeI to form 200 to 300 bp of an insert, and then the insert was inserted into a vector. Also, according to previous reports showing that gene silencing caused by viruses was caused by the position and size of the inserted gene, the pds gene of melon disclosed in the NCBI Genbank was 1904 bp, a primer capable of constructing a fragment by attaching a region near the 5'-terminus, a region near the 3'-terminus, and genes in two regions in a coding region even in watermelon was constructed with reference to the nucleotide sequence of the pds gene to be used to amplify cDNA synthesized from RNA of each plant, the cDNA was also cleaved with XhoI-PmeI, and each resulting fragment was inserted and inoculated, thereby confirming efficiency of gene silencing (FIG. 8).

<Example 9-2> Application of Gene Silencing to Leaves

Figure 9:
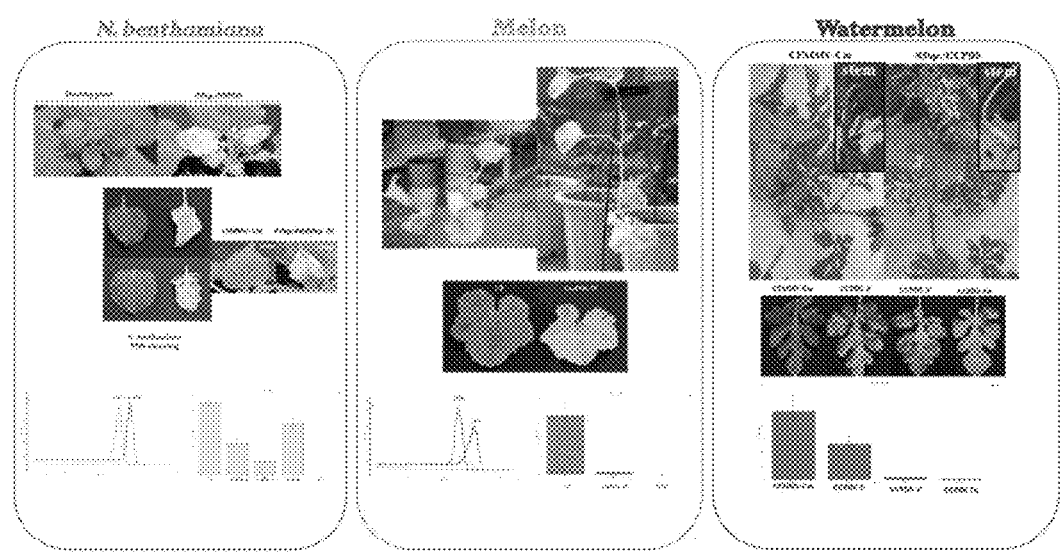
FIG. 9 shows a relative quantification result to show the suppression of pds gene mRNA expression in leaves by real-time qPCR by extracting phenotypes and RNAs of *N. benthamiana*, melon, and watermelon according to the suppression of pds gene expression. In watermelon, efficiency difference is shown according to a gene amplification position and an inserting method.

Due to the decreased expression level of the pds gene, phenotypes of whitening of leaves by photo-bleaching were identified in *N. benthamiana*, melon, cucumber and watermelon were confirmed, and different results were shown according to a gene insertion method. Whitening caused by pds gene silencing was maintained until the growth was completed (FIG. 9).

<Example 9-3> Application of Gene Silencing to Fruit

Figure 10:
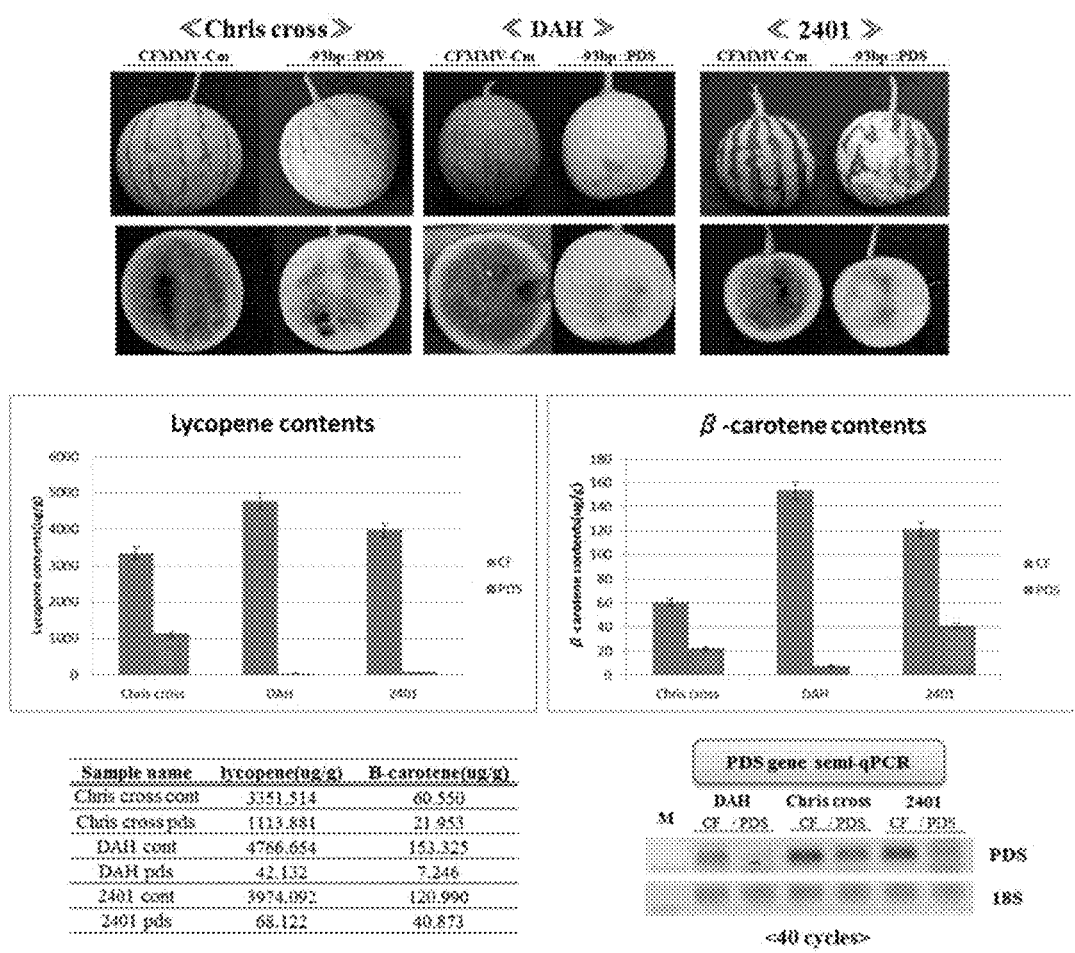
FIG. 10 shows a relative quantification result obtained by semi qRT-PCR to show suppression of mRNA expression of pds gene in leaves by extracting phenotypes and RNAs from fruit flesh of three types of watermelon cultivars according to the suppression of pds gene expression, and contents of β-carotene and lycopene, measured by HPLC.

A Pds gene encodes an enzyme constituting a β-carotene biosynthesis pathway, which is an early-stage enzyme of lycopene. Therefore, due to silencing of the pds gene, whitening of red fruit flesh, without lycopene, in watermelon was observed, and positive results were obtained from all of the three types of cultivars. Accordingly, a result which can be stably applied is provided as a means for gene function analysis in fruits (FIG. 10).

<Example 9-4> Real-Time qPCR for Confirming Gene Silencing at RNA Level

A whitened (photo-bleached) leaf sample was harvested to extract RNA, and cDNA was synthesized using superscript III reverse transcriptase and oligo dT, and the suppression of pds gene expression was confirmed through real-time qPCR. As a gene for normalization, 18S rRNA gene was used in Cucurbitaceae plants, and a primer was constructed from a part of the pds gene to be used in a comparative quantification. The real-time qPCR was performed using total 20 μl of a reaction mixture including the following substances: 2 μl of first chain cDNAs, 2× master mix, and 20× Evagreen dye (Biofact Co.). PCR was performed under the following temperature conditions: 40 cycles of 94° C. for 12 minutes, 94° C. for 10 seconds, and 60° C. for 30 seconds. As a result, it was confirmed that gene expression levels were decreased in all plants, and when an experiment according to a method of inserting a target gene fragment in watermelon was performed, gene expression was most efficiently suppressed in a subject inoculated with fragments at both positions (FIG. 9).

<Example 9-5> Analyses of Lycopene and Beta-Carotene Contents in Fruits 45 dap (day after pollination) of watermelon was harvested to obtain 15 g of fruit flesh, followed by instantly freezing in liquid nitrogen and freeze-drying for one week.

1. Pretreatment of Samples 0.1 g of watermelon cut finely using a blender was put into a screw tap tube, and then beads and samples were added at a ratio of 1:1. Following addition of 1 ml of 0.5 mM BHT-added ethanol, the resulting mixture was put into a bead buffer and then vigorously stirred for 2.5 minutes. The ethanol, sample, and beads in the tube were all transferred to a 15 ml tube, and everything left in the screw tap tube was washed with 1 ml acetone three times and transferred to a 15 ml tube. 3 ml of petrol ether was added to the tube and vortexed, followed by adding 8 ml of 20% NaCl and vortexing. The resulting mixture was centrifuged at 3000 rpm for 10 minutes, and only the supernatant was harvested. After the increase in a sample mass, $Na_2SO_4$ was added to the sample, and then the sample was passed through a filter (PTFE, 13 mm, 0.2 μm; Advantec, U.S.A.) to finally prepare an analyte.

2. Quantitative Analysis of Carotenoid Using Liquid Chromatography

A carotenoid content was quantified using a liquid chromatography system (Waters 2489; Waters, U.S.A.) equipped with a reversed-phase column (Kinetex 2.6 μm, C18 100 A, 100×4.60 mm; Phenomenex, U.S.A.). Mobile phase A was 78% methanol, and mobile phase B was 100% ethyl acetate. Separation conditions included 0-10 min, 70% B; 10-14 min, 100% B; 14-14.01 min, 0% B; and 14.01-20 min, 0% B, and a flow rate was 1 ml per minute. As a standard for quantification, β-carotene and lycopene (Sigma-Aldrich Co., U.S.A.) were used, and optical densities were measured at 450 nm and 660 nm to quantify the total content of carotenoid.

From three types of cultivars such as pCF93-pds-infected chris cross, DAH and 2401, it was confirmed that the accumulation of β-carotene and lycopene was decreased by a factor three to 110 compared to that of CFMMV-infected watermelon (FIG. 10).

Figure 12:
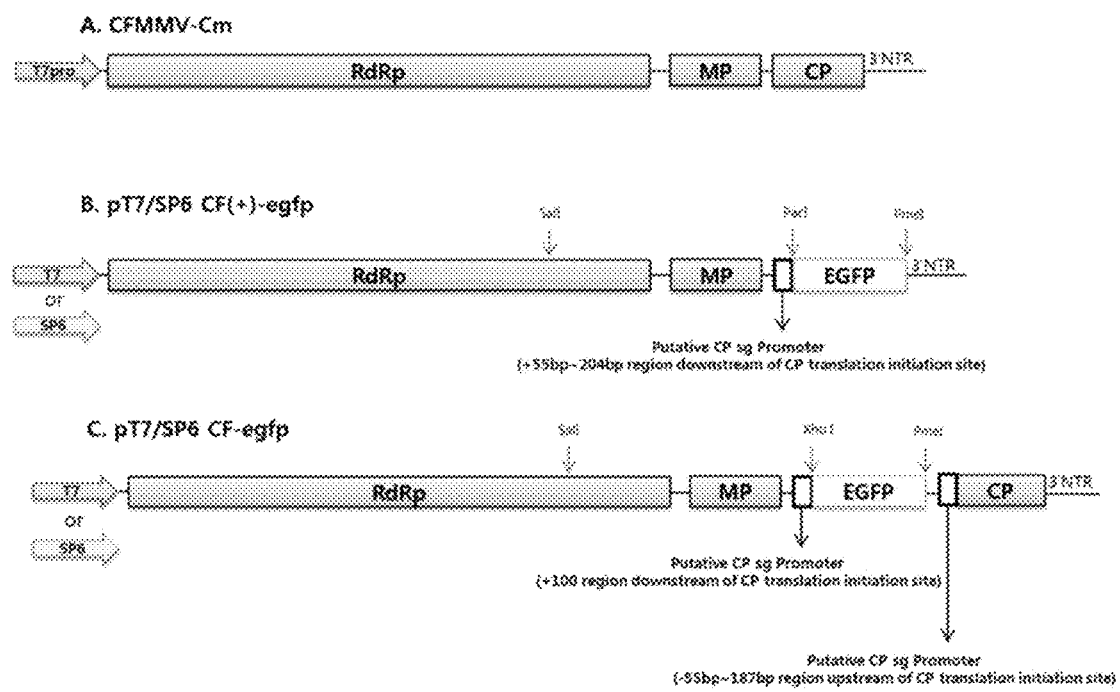
FIG. 12 is a schematic diagram of a CFMMV vector including T7 and SP6 promoters.
Figure 1A:
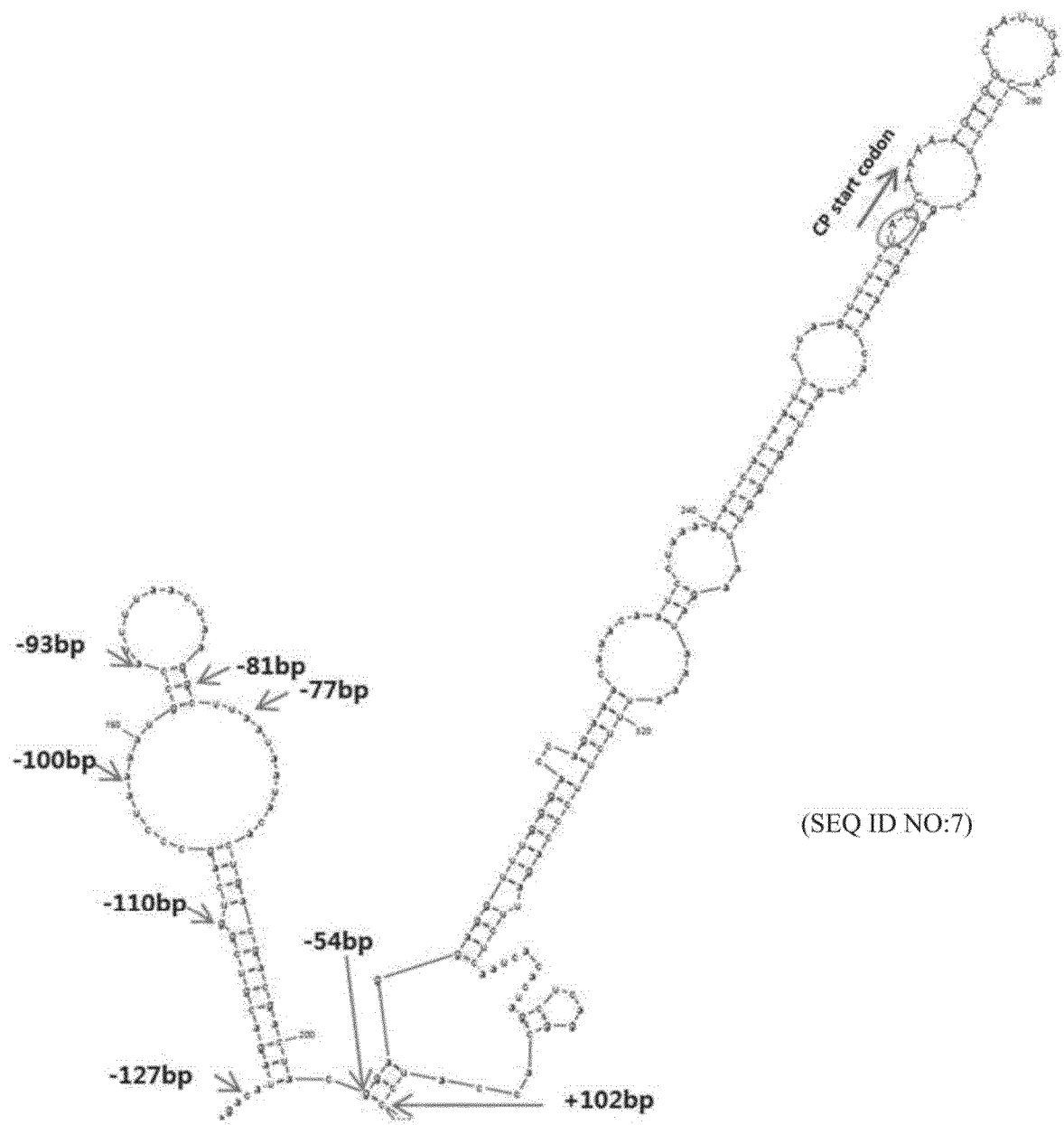

<Example 10> Construction and Inoculation of CFMMV Vector Including T7 Promoter and SP6 Promoter CP SGP of the virus was first designed in the range of +55 bp based on a 2D structure result. Using pT7CF-Cm$_{flc}$ as a basic backbone, CP was removed, 3'NTR was primarily inserted to create MluI and PmeI sites, and, while the initiation of translation was suppressed by substituting the start codon ATG into AAG to determine the SGP range, the created gene was amplified by PCR and inserted to include only a desired range of SGP to prepare Pad. Accordingly, MCS including PacI-MluI-PmeI was constructed, a SphI-linearized vector was inoculated through in vitro transcription by inserting EGFP with the Pad and PmeI previously formed using a mMASSAGE mMACHINE kit (Ambion). In order to construct a vector including the coat protein, a vector using an upstream subgenomic promoter range of +100 bp and including a subgenomic promoter range corresponding to −55 bp to −204 bp from the start codon of the coat protein was constructed, and in this process, like the structure of a vector including a 35S promoter, restriction sites were changed to XhoI-PmeI, and the sequence of the start codon was also changed to ATG→ACG to construct a vector. The result and structure of the vector are shown in FIGS. 12 and 13.

SEQUENCE LISTING

```
<160> NUMBER OF SEQ ID NOS: 6

<210> SEQ ID NO 1
<211> LENGTH: 6571
<212> TYPE: DNA
<213> ORGANISM: Cucumber fruit mottle mosaic virus

<400> SEQUENCE: 1
gataaaagtt ttttacattg aacaaaaaca atatacatta cttttataac aatacacaat      60
acatggcaaa cattacaaaa catatcaatg ataccaggga ggctgcggcc gccgggcgta     120
atccgctcgt ggcgcagctg gcttcgaaga gggtttatga tgaggctgtc aagtctcttg     180
attctcaaga taaacgccct aaggtgaatt ttgctcgggt attgaccaca gagcagacga     240
ggaaggtcac ggagtcgtat ccggagtttt cgatcagtta tactgcgtcg gccttatccg     300
tgcatagctt ggcggggga ctgcgatatt tagaaggtga gtacctgatg atgcaggttc     360
cctatgggtc gcccgtgtat gatatcggag ggaatttctc gcaacatatg ctgaagggga     420
gagcatacgt gcactcctgc aatccgtgcc tggacctgaa ggacattgca cgcaatgaga     480
tgtacaagga tgccattgac cgttatgtgc ataagaaacg cgaagcgcca cgttctaatg     540
cttggagggc tagggcagag tcgtctaatg aaattaagac ggccggtcta ccttcatggc     600
agatcgatgc gtttcagcga tataaggatt gtccagaggc ggtcacctgt aatgatgtgt     660
tccaagagtg tcagtatgaa catacgagga gagggatcg ttatgcagtt gctctgcatt     720
cgatttatga tattcctttc gaacagatag gacctgcgct cttgcggaag aatattaagg     780
ttctcttcgc cgcattccat ttctcagagg agttgctgtt ggggcaaagt tttggtgcct     840
tgcctaatat aggtgcgttc tttaccgtca atggtgattc cgttgagttt cagttcgaag     900
aagaatctac tttgcattat tcacatagtt tccagaatat taggaagata gtaactagga     960
cgtattttcc tgcttcagat agggtagttt atgtaaagga gtttatggtt aagcgtgtag    1020
atactttctt tttccgtatg gttaggggttg atacccatat gttacataag tcagtaggta    1080
cgtatcctgt ttgtgcgact aactatttct ctctcaagtc gtcaccaata tttcaggata    1140
```

```
aagccacgtt ctctgtgtgg tttcccaaag ctaaatctaa ggtggtgata cctatctta    1200 agatgcaagg gtttttcact gggtctattg tggcagagaa gatgatgatc gatgctagct   1260
ttattcatac tgttatcaat catatctgta cttatgataa taaggcgtta acgtggagga   1320
atgttcagtc cttcgtcgag tcaattcggt cccgggttgt cgtgaatggg gtttcggtgc   1380
ggagtgaatg ggatgtgccg gtagagcttt taactgatat ttcgttcacc gttttttac    1440 tagtcaaagt taagaagacg cagatcgaga ttatgagtga taaaattgtg acacaacctc   1500
aggggttgat tgagcggatt gtacagagag tctctgaagc tttcgaagga tgtacagaag   1560
tggtgcaaaa ggcccttctt acttccgggt ggttcagaac tccagcggat gatctcgttc   1620
ttgatattcc tgagttgttc atggattttc atgattatct cagcggtgtc ttcgaagcgg   1680
atgctcgtat tgaggcaacg gacgtcgaag atgttttgag tgcttccgac aagctttatt   1740
cgactgtatc ggagctttgt gagcgatatt ctgggattga atttgacttg gagaagtttt   1800 ctgattttg ccaccaccat gacgtgaatc ctgctttggt gggaaccgtg atagaggcga    1860
ttttttcgca gactgccggg attacagtca ctgggctgtc tacaaaatct gttgagtggg   1920
cagccgcaga ggctttagca ccgacgtctg ttgatatgga ttgtgacagt gatgatgagg   1980
agctggagca gaaattcccg aatctgtcca atgaggagtt gagatatttg catgaggtga   2040
gatcgaagga agccgctttc ttggagctac aagatacatt taaaaccaag aaggtgactg   2100
agttagtgtc tgtgggagta ggagctttgc caacgctacc gcgtcagtgg atagcgacag   2160
ggaaggttca tcttcctcag gttggtctgt cggttgggaa gaataaacat tcggtcgaga   2220
tatgtgacga agatggggtc agtgtgaaga atctgcatct gacggagacg tgtaatctaa   2280
gattgaagaa gactatcact ccggtgatct atactgggcc cataagagtg cgtcagatgg   2340
ctaattatct cgattatctt tctgctaatc tggccgctac gataggaaat ctcgaaagaa   2400
ttgttcgatc gaattggtct ggggaggatg aggttgtgca aacttatggt ctttttgatt   2460
gtcaggctaa taagtggatc ttactgccct ctgagaaaac acatagttgg ggtgtctgtc   2520
tgactatgga tgataagctt cgtgttgtcc tgctgcagta tgattccgcc ggttggccga   2580
ttgtagataa gtcttttttgg aaagctttt gtgtgtgtgc ggatactaaa gttttttctg    2640
ttattaggag tcttgaggtt ttgtctgctt tacctttagt tgaaccggat gctaagtatg   2700
tgctgattga tggtgtgcct ggttgtggga agacgcaaga gattatatcg agtgcggact   2760
tcaaaacgga tctaatcctt acacctggta aggaagccgc ggccatgatc aggcgtagag   2820
ccaacatgaa atataggagt cccgtcgcca caaatgataa tgtgaggact tttgattcat   2880
ttgtaatgaa taaaaagccc tttacctta agacactatg ggtggatgag gtctcatgg    2940 tgcataccgg tctgttaaat ttctgtgtga atattgctaa ggtaaggaa gttcgtattt     3000 tcggtgatac taagcaaatc cccttcatta atagagtgat gaatttcgat tacccactag   3060
agctgaggaa aattattgtt gatacggtgg aaaagcggta cacgagtaaa cggtgtccaa   3120
gggatgtgac tcattatttg aatgaggtat attccagtcc cgtgtgtact actagtcctg   3180
tcgtacattc agttaccaca aaaaagattg ctggagtggg tcttttgcga ccggaattga   3240
cggcattgcc tggtaagatt ataactttca ctcagaatga caagcaaacg cttttaaaag   3300
cgggttatgc tgatgtgaat actgtgcatg aggtgcaggg ggagacatat gaggaaactt   3360
ccgtggtgag ggctactgct acaccaatcg gtttgatttc gcgtaagtct ccgcatgtgc   3420
ttgttgctct gtcgaggcat accaaggcga tgacgtatta tactgtgact gtggatcccg   3480
```

```
tgagctgtat aattgctgat ttggagaagg tcgatcaaag tattctgtct atgtatgcct   3540
ctgtggcggg gaccaaatag caattacagc aactatccgt ctatgtgcat caaaatttgg   3600
ttttgcccgt gtcgaaggcg ggttttgga cggatatgca gaattttat gacgcttgtc     3660 tgcccgggaa tagttttgtg ttgaatgatt acgattctgt gactatgcgg ctggttgata   3720
atgagatcaa cctgcaacct tgtaggttaa ctctatctaa agccgatcct gttacagagt   3780
ctctgaagat ggagaaaaag gagttttga tcccgcttgt taaaactgct acggagcgtc    3840
cgcggatccc tgggctttta gagaatttga tagctatagt taagaggaat tttaataccc   3900
cggatttagc cgggagttta gatatttcta gtattagtaa gggtgtagta gataacttct   3960
tttccacttt tttgcgtgac gagcaattgg cggatcacct ttgtaaagtt aggtctctta   4020
gtctagagtc ttttccgca tggtttgata atcagtcaac ttgtgctctg gtcagttgt    4080 ctaatttcga ttttgtggat ctgcctcccg ttgatgttta taatcatatg attaagaggc   4140
aacccaaatc gaagttagac acctcgattc agtctgagta tcctgcgttg caaacgattg   4200
tttatcatag taaattagtg aatgcggttt ttggtcccgt tttccgttat cttacttccg   4260 agttttatc tatggtagat aatagtaaat ttttctttta tactaggaaa actccggatg    4320
atttgcaaag tttcttttcc acacttcca ataagcagga gtatgagatt ttagagctag    4380
atgtttccaa atatgataaa tcacagaatg attttcatca ggctgtggag atgcttattt   4440
gggaacgttt aggtctagat gatattcttg ctaggatttg ggaaatgggg cataagaaga   4500
cgcatatcag tgatttccaa gctgggatta aaactcttat ttattatcag cggaaatctg   4560
gagatgttac tacttttata ggtaatactt ttattatagc tgcttgtgtc gcttctatgg   4620
ttccgctgag tcggagtttc aaagctgcct tttgtggtga tgattcactg atttatatgc   4680
caccgaatct ggaatataat gacatacagt cgaccgcgaa tctcgtgtgg aatttcgagg   4740
ctaaactgta taagaagaaa tatggttatt tctgtggcaa atatgtgatc catcatgcga   4800
atgggtgtat tgtttatccg gatccgttga agctaatttc taaattaggc aataagagtc   4860
tggaaagtta cgatcatttg gaggaattta ggatttctct gatggacgta gctaaacctt   4920
tgttcaatgc tgcttatttt catcttttag atgatgctat ccacgagtat tttcctagtg   4980
ttgggggtag cacgtttgct attagttctt tgtgcaagta tcttagtaat aagcagttgt   5040
ttaggtctct attcattaag cctagtgtct agatgtccat tagtaaggtc ggtgtcagga   5100
acgctttaaa gccagaggaa tttgttaaga ttacttgggt tgataagcta cttcctgatg   5160
cttttactat tcttaagtat ttatctatta cagattatag tgttgtacag tctaaagact   5220
atgaacatct catacctgtg gatctactac gtggcgtgga tttttcaaag tctaaatatg   5280
ttactttggt tggtgttgtg atttccgggg tctggacaat tcctgagaat tgtgccggtg   5340
gtgctaccgt ggcgctggtc gatactcgga tgtccttagt gtcggagggt actatttgta   5400
agttttctgt atctgcagcc agtcgggatt ttacggtaaa attgattccg aattattatg   5460
tgactgctgc tgatgcctcc tccaaaccct ggtctttgtt tgttaggatt tctggtgtta   5520
ggatcaaaga tggtttttct ccgttaactc tggagattgc ctctttggtg gctaccacca   5580
attctatttt aaagaagggt ctaagagtta gtgtgatcga gtccgtggta gggtctgatg   5640
cctccgtgtc gttggatacc ttgtctgaaa aggttcaacc cttttttgat tcggttccga   5700
ttacggcttc agtggtatct cgtgataggt cttatgtgtc taaaggtcgc cctccttctc   5760
ggagtggacc tgtgtcgcgt aaatctaaaa gtaagagtga ggcagaatct ttttcggata   5820
gtggcgcttc tgagccacta agttcataat caagatgtct tactctactt ctggtttgcg   5880
```

```
ttctttgcct gcatatacta agtcttttg tccttattat gctttgtatg atctgttggt    5940
gtcagcccaa ggtggagccc tgcaaacgca aaatggtaaa gacattttgc gtgactccat    6000
aaatggggtg ttaacgacag ttgcgtctcc tacgagtcgg ttccctgcgg aagggttctt    6060
tgtctggtcc cgtgagtcgc gcattgctgc tatattagat tctctgcttt cggcgttgga    6120
ttcaagaaat agggctattg aagttgaaaa cccttctaat ccttcgacca gtgaagcttt    6180
gaatgctact aagcgcaatg acgacgcgtc tactgctgcg cacaacgaca ttcctcagct    6240
gatttcagct ttgaatgacg gtgccggtgt gtttgataga gcgtcttttg agagtcagtt    6300
cggtctagta tggaccgctg cgtcgtcgtc tacctcgaag tgaggcgtgg tcgctgcgtt    6360
aagcgataga gtttttccct cctctttaat cgaagggttt cccgttatgg gcgtggtcat    6420
cacgaaagat gatagagttt ttccctcctc ttaaatcgaa gggattgttt gcgcggtttc    6480
taccgagcct ctgctgtgtg acagtaagct ggcgtaagca attatgggta gaggtgttcg    6540
aatcaccccc tttgccccgg gtaggggccc a                                  6571

<210> SEQ ID NO 2
<211> LENGTH: 193
<212> TYPE: DNA
<213> ORGANISM: Artificial Sequence
<220> FEATURE:
<223> OTHER INFORMATION: Chemically Synthesized

<400> SEQUENCE: 2
gagtggacct gtgtcgcgta aatctaaaag taagagtgag gcagaatctt tttcggatag      60
tggcgcttct gagccactaa gttcataatc aagatgtctt actctacttc tggtttgcgt     120
tctttgcctg catatactaa gtctttttgt ccttattatg ctttgtatga tctgttggtg     180
tcagcccaag gtg                                                        193

<210> SEQ ID NO 3
<211> LENGTH: 7498
<212> TYPE: DNA
<213> ORGANISM: Artificial Sequence
<220> FEATURE:
<223> OTHER INFORMATION: Chemically Synthesized

<400> SEQUENCE: 3
gataaaagtt ttttacattg aacaaaaaca atatacatta cttttataac aatacacaat      60
acatggcaaa cattacaaaa catatcaatg ataccaggga ggctgcggcc gccgggcgta     120
atccgctcgt ggcgcagctg gcttcgaaga gggtttatga tgaggctgtc aagtctcttg     180
attctcaaga taaacgccct aaggtgaatt ttgctcgggt attgaccaca gagcagacga     240
ggaaggtcac ggagtcgtat ccggagtttt cgatcagtta tactgcgtcg gccttatccg     300
tgcatagctt ggcgggggga ctgcgatatt tagaaggtga gtacctgatg atgcaggttc     360
cctatgggtc gcccgtgtat gatatcggag ggaatttctc gcaacatatg ctgaagggga     420
gagcatacgt gcactcctgc aatccgtgcc tggacctgaa ggacattgca cgcaatgaga     480
tgtacaagga tgccattgac cgttatgtgc ataagaaacg cgaagcgcca cgttctaatg     540
cttggagggc tagggcagag tcgtctaatg aaattaagac ggccggtcta ccttcatggc     600
agatcgatgc gtttcagcga tataaggatt gtccagaggc ggtcacctgt aatgatgtgt     660
tccaagagtg tcagtatgaa catacgagga gagggatcg ttatgcagtt gctctgcatt     720
cgatttatga tattcctttc gaacagatag gacctgcgct cttgcggaag aatattaagg     780
```

```
ttctcttcgc cgcattccat ttctcagagg agttgctgtt ggggcaaagt tttggtgcct      840
tgcctaatat aggtgcgttc tttaccgtca atggtgattc cgttgagttt cagttcgaag      900
aagaatctac tttgcattat tcacatagtt tccagaatat taggaagata gtaactagga      960 cgtatttttcc tgcttcagat agggtagttt atgtaaagga gtttatggtt aagcgtgtag    1020
atactttctt tttccgtatg gttagggttg atacccatat gttacataag tcagtaggta    1080
cgtatcctgt ttgtgcgact aactatttct ctctcaagtc gtcaccaata tttcaggata    1140
aagccacgtt ctctgtgtgg tttcccaaag ctaaatctaa ggtggtgata cctatcttta    1200
agatgcaagg gttttttcact gggtctattg tggcagagaa gatgatgatc gatgctagct   1260
ttattcatac tgttatcaat catatctgta cttatgataa taaggcgtta acgtggagga    1320
atgttcagtc cttcgtcgag tcaattcggt cccgggttgt cgtgaatggg gtttcggtgc    1380
ggagtgaatg ggatgtgccg gtagagcttt taactgatat ttcgttcacc gttttttttac  1440 tagtcaaagt taagaagacg cagatcgaga ttatgagtga taaaattgtg acacaacctc    1500 agggggttgat tgagcggatt gtacagagag tctctgaagc tttcgaagga tgtacagaag   1560
tggtgcaaaa ggcccttctt acttccgggt ggttcagaac tccagcggat gatctcgttc    1620
ttgatattcc tgagttgttc atggattttc atgattatct cagcggtgtc ttcgaagcgg    1680
atgctcgtat tgaggcaacg gacgtcgaag atgttttgag tgcttccgac aagctttatt    1740
cgactgtatc ggagctttgt gagcgatatt ctgggattga atttgacttg gagaagtttt    1800 ctgattttg ccaccaccat gacgtgaatc ctgctttggt gggaaccgtg atagaggcga     1860 tttttttcgca gactgccggg attacagtca ctgggctgtc tacaaaatct gttgagtggg    1920
cagccgcaga ggctttagca ccgacgtctg ttgatatgga ttgtgacagt gatgatgagg    1980
agctggagca gaaattcccg aatctgtcca atgaggagtt gagatatttg catgaggtga    2040
gatcgaagga agccgctttc ttggagctac aagatacatt taaaaccaag aaggtgactg     2100
agttagtgtc tgtgggagta ggagcttttgc caacgctacc gcgtcagtgg atagcgacag    2160
ggaaggttca tcttcctcag gttggtctgt cggttgggaa gaataaacat tcggtcgaga    2220
tatgtgacga agatggggtc agtgtgaaga atctgcatct gacggagacg tgtaatctaa    2280
gattgaagaa gactatcact ccggtgatct atactgggcc cataagagtg cgtcagatgg    2340
ctaattatct cgattatctt tctgctaatc tggccgctac gataggaaat ctcgaaagaa    2400
ttgttcgatc gaattggtct ggggaggatg aggttgtgca aacttatggt cttttttgatt  2460 gtcaggctaa taagtggatc ttactgcccct ctgagaaaac acatagttgg ggtgtctgtc   2520
tgactatgga tgataagctt cgtgttgtcc tgctgcagta tgattccgcc ggttggccga    2580
ttgtagataa gtcttttttgg aaagcttttt gtgtgtgtgc ggatactaaa gttttttctg   2640
ttattaggag tcttgaggtt ttgtctgctt tacctttagt tgaaccggat gctaagtatg    2700
tgctgattga tggtgtgcct ggttgtggga agacgcaaga gattatatcg agtgcggact    2760
tcaaaacgga tctaatcctt acacctggta aggaagccgc ggccatgatc aggcgtagag    2820
ccaacatgaa atataggagt cccgtcgcca caaatgataa tgtgaggact tttgattcat    2880
ttgtaatgaa taaaaagccc tttacccttta agacactatg ggtggatgag ggtctcatgg   2940
tgcataccgg tctgttaaat ttctgtgtga atattgctaa ggtaaaggaa gttcgtatttt  3000 tcggtgatac taagcaaatc cccttcatta atagagtgat gaatttcgat tacccactag    3060
agctgaggaa aattattgtt gatacggtgg aaaagcggta cacgagtaaa cggtgtccaa    3120
gggatgtgac tcattatttg aatgaggtat attccagtcc cgtgtgtact actagtcctg    3180
```

```
tcgtacattc agttaccaca aaaaagattg ctggagtggg tcttttgcga ccggaattga    3240
cggcattgcc tggtaagatt ataactttca ctcagaatga caagcaaacg cttttaaaag    3300
cgggttatgc tgatgtgaat actgtgcatg aggtgcaggg ggagacatat gaggaaactt    3360
ccgtggtgag ggctactgct acaccaatcg gtttgatttc gcgtaagtct ccgcatgtgc    3420
ttgttgctct gtcgaggcat accaaggcga tgacgtatta tactgtgact gtggatcccg    3480
tgagctgtat aattgctgat ttggagaagg tcgatcaaag tattctgtct atgtatgcct    3540
ctgtggcggg gaccaaatag caattacagc aactatccgt ctatgtgcat caaaatttgg    3600
ttttgcccgt gtcgaaggcg ggttttttgga cggatatgca gaattttttat gacgcttgtc    3660 tgcccgggaa tagttttgtg ttgaatgatt acgattctgt gactatgcgg ctggttgata    3720
atgagatcaa cctgcaacct tgtaggttaa ctctatctaa agccgatcct gttacagagt    3780
ctctgaagat ggagaaaaag gagttttttga tcccgcttgt taaaactgct acggagcgtc    3840
cgcggatccc tgggctttta gagaatttga tagctatagt taagaggaat tttaataccc    3900
cggatttagc cgggagttta gatatttcta gtattagtaa gggtgtagta gataacttct    3960
tttccacttt tttgcgtgac gagcaattgg cggatcacct tgtaaagtt aggtctctta    4020 gtctagagtc ttttttccgca tggtttgata atcagtcaac ttgtgctctg ggtcagttgt    4080
ctaatttcga ttttgtggat ctgcctcccg ttgatgttta taatcatatg attaagaggc    4140
aacccaaatc gaagttagac acctcgattc agtctgagta tcctgcgttg caaacgattg    4200
tttatcatag taaattagtg aatgcggttt ttggtcccgt tttccgttat cttacttccg    4260 agttttatc tatggtagat aatagtaaat ttttcttta tactaggaaa actccggatg    4320
atttgcaaag tttcttttcc cactttcca ataagcagga gtatgagatt ttagagctag    4380
atgtttccaa atatgataaa tcacagaatg attttcatca ggctgtggag atgcttattt    4440
gggaacgttt aggtctagat gatattcttg ctaggatttg ggaaatgggg cataagaaga    4500
cgcatatcag tgatttccaa gctgggatta aaactcttat ttattatcag cggaaatctg    4560
gagatgttac tacttttata ggtaatactt ttattatagc tgcttgtgtc gcttctatgg    4620
ttccgctgag tcggagtttc aaagctgcct tttgtggtga tgattcactg atttatatgc    4680
caccgaatct ggaatataat gacatacagt cgaccgcgaa tctcgtgtgg aatttcgagg    4740
ctaaactgta taagaagaaa tatggttatt tctgtggcaa atatgtgatc catcatgcga    4800
atgggtgtat tgtttatccg gatccgttga agctaatttc taaattaggc aataagagtc    4860
tggaaagtta cgatcatttg gaggaattta ggatttctct gatggacgta gctaaacctt    4920
tgttcaatgc tgcttatttt catcttttag atgatgctat ccacgagtat tttcctagtg    4980
ttgggggtag cacgtttgct attagttctt tgtgcaagta tcttagtaat aagcagttgt    5040
ttaggtctct attcattaag cctagtgtct agatgtccat tagtaaggtc ggtgtcagga    5100
acgctttaaa gccagaggaa tttgttaaga ttacttgggt tgataagcta cttcctgatg    5160
cttttactat tcttaagtat ttatctatta cagattatag tgttgtacag tctaaagact    5220
atgaacatct catacctgtg gatctactac gtggcgtgga ttttttcaaag tctaaatatg    5280 ttactttggt tggtgttgtg atttccgggg tctggacaat tcctgagaat tgtgccggtg    5340
gtgctaccgt ggcgctggtc gatactcgga tgtccttagt gtcggagggt actatttgta    5400
agttttctgt atctgcagcc agtcgggatt ttacggtaaa attgattccg aattattatg    5460
tgactgctgc tgatgcctcc tccaaaccct ggtctttgtt tgttaggatt tctggtgtta    5520
```

-continued

```
ggatcaaaga tggttttttct ccgttaactc tggagattgc ctctttggtg gctaccacca    5580
attctatttt aaagaagggt ctaagagtta gtgtgatcga gtccgtggta gggtctgatg    5640
cctccgtgtc gttggatacc ttgtctgaaa aggttcaacc cttttttgat tcggttccga    5700
ttacggcttc agtggtatct cgtgataggt cttatgtgtc taaaggtcgc cctccttctc    5760
ggagtggacc tgtgtcgcgt aaatctaaaa gtaagagtga ggcagaatct ttttcggata    5820
gtggcgcttc tgagccacta agttcataat caagacgtct tactctactt ctggtttgcg    5880
ttctttgcct gcatatacta agtcttttg tccttattat gctttgtatg atctgttggt    5940
gtcagcccaa ggtgctcgag atggtgagca agggcgagga gctgttcacc ggggtggtgc    6000
ccatcctggt cgagctggac ggcgacgtaa acggccacaa gttcagcgtg tccggcgagg    6060
gcgagggcga tgccacctac ggcaagctga ccctgaagtt catctgcacc accggcaagc    6120
tgcccgtgcc ctggcccacc ctcgtgacca ccctgaccta cggcgtgcag tgcttcagcc    6180
gctaccccga ccacatgaag cagcacgact tcttcaagtc cgccatgccc gaaggctacg    6240
tccaggagcg caccatcttc ttcaaggacg acggcaacta caagacccgc gccgaggtga    6300
agttcgaggg cgacaccctg gtgaaccgca tcgagctgaa gggcatcgac ttcaaggagg    6360
acggcaacat cctggggcac aagctggagt acaactacaa cagccacaac gtctatatca    6420
tggccgacaa gcagaagaac ggcatcaagg tgaacttcaa gatccgccac aacatcgagg    6480
acggcagcgt gcagctcgcc gaccactacc agcagaacac ccccatcggc gacggccccg    6540
tgctgctgcc cgacaaccac tacctgagca cccagtccgc cctgagcaaa gaccccaacg    6600
agaagcgcga tcacatggtc ctgctggagt tcgtgaccgc cgccgggatc actctcggca    6660
tggacgagct gtacaagtaa gtttaaacga gtggacctgt gtcgcgtaaa tctaaaagta    6720
agagtgaggc agaatctttt tcggatagtg gcgcttctga gccactaagt tcataatcaa    6780
gatgtcttac tctacttctg gtttgcgttc tttgcctgca tatactaagt cttttgtcc    6840
ttattatgct ttgtatgatc tgttggtgtc agcccaaggt ggagccctgc aaacgcaaaa    6900
tggtaaagac attttgcgtg actccataaa tgggttgtta acgacagttg cgtctcctac    6960
gagtcggttc cctgcggaag ggttctttgt ctggtcccgt gagtcgcgca ttgctgctat    7020
attagattct ctgctttcgg cgttggattc aagaaatagg gctattgaag ttgaaaaccc    7080
ttctaatcct tcgaccagtg aagctttgaa tgctactaag cgcaatgacg acgcgtctac    7140
tgctgcgcac aacgacattc ctcagctgat ttcagctttg aatgacggtg ccggtgtgtt    7200
tgatagagcg tcttttgaga gtcagttcgg tctagtatgg accgctgcgt cgtcgtctac    7260
ctcgaagtga ggcgtggtcg ctgcgttaag cgatagagtt tttccctcct ctttaatcga    7320
agggtttccc gttatgggcg tggtcatcac gaaagatgat agagttttc cctcctctta    7380
aatcgaaggg attgtttgcg cggtttctac cgagcctctg ctgtgtgaca gtaagctggc    7440
gtaagcaatt atgggtagag gtgttcgaat cacccccttt gccccgggta ggggccca     7498
```

<210> SEQ ID NO 4
<211> LENGTH: 751
<212> TYPE: DNA
<213> ORGANISM: Artificial Sequence
<220> FEATURE:
<223> OTHER INFORMATION: Chemically Synthesized

<400> SEQUENCE: 4

```
gtcaacatgg tggagcacga cactctcgtc tactccaaga atatcaaaga tacagtctca      60
gaagaccaga gggctattga acttttcaa caaagggtaa tatcgggaaa cctcctcgga     120
```

```
ttccattgcc cagctatctg tcacttcatc gaaaggacag tagaaaagga agatggcttc    180
tacaaatgcc atcattgcga taaaggaaag gctatcgttc aagatgcctc taccgacagt    240
ggtcccaaag atggaccccc acccacgagg aacatcgtgg aaaaagaaga cgttccaacc    300
acgtcttcaa agcaagtgga ttgatgtgat ggtcaacatg gtggagcacg acactctcgt    360
ctactccaag aatatcaaag atacagtctc agaagaccag agggctattg agacttttca    420
acaaagggta atatcgggaa acctcctcgg attccattgc ccagctatct gtcacttcat    480
cgaaaggaca gtagaaaagg aagatggctt ctacaaatgc catcattgcg ataaaggaaa    540
ggctatcgtt caagatgcct ctaccgacag tggtcccaaa gatggacccc cacccacgag    600
gaacatcgtg gaaaaagaag acgttccaac cacgtcttca aagcaagtgg attgatgtga    660
tatctccact gacgtaaggg atgacgcaca atcccactat ccttcgcaag accttcctc    720 tatataagga agttcatttc atttggagag g                                    751

<210> SEQ ID NO 5
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 5
taatacgact cactatagg                                                   19

<210> SEQ ID NO 6
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 6
atttaggtga cactatag                                                    18
```

The invention claimed is:

1. A nucleic acid molecule comprising a subgenomic promoter comprising the nucleotide sequence from −204 bp to +160 bp from a start codon of the coat protein of Cucumber fruit mottle mosaic virus (CFMMV) operably linked to a heterologous nucleotide sequence.

2. The nucleic acid molecule of claim 1, wherein the CFMMV genome comprises the nucleotide sequence of SEQ. ID. NO: 1.

3. The nucleic acid molecule of claim 1, wherein the start codon of the coat protein of the CFMMV is located at nucleotides from 5855 to 5857 of the CFMMV genome of SEQ. ID. NO: 1.

4. The nucleic acid molecule of claim 1, wherein the subgenomic promoter comprises a nucleotide sequence from one selected from the group consisting of −204, −187, −180, −170, −163, −157, −152, −148, −143, −135, −127, −121, −110, −100, −93, −81, −77, −55 and −30 bp to +160 bp from the start codon of the coat protein.

5. The nucleic acid molecule of claim 1, wherein the subgenomic promoter comprises the nucleotide sequence from −93 bp to +100 bp from the start codon of the coat protein.

6. The nucleic acid molecule of claim 5, wherein the subgenomic promoter comprises the nucleotide sequence of SEQ. ID. NO: 2.

7. A Cucumber fruit mottle mosaic virus (CFMMV) vector, comprising the nucleic acid molecule of claim 1.

8. The CFMMV vector of claim 7, wherein the vector shows a gene silencing or gene expression effect in Cucurbitaceae plants.

9. The CFMMV vector of claim 7, wherein the vector comprises the nucleotide sequence of SEQ. ID. NO: 3.

10. The CFMMV vector of claim 7, wherein the vector further comprises a T7, SP6 or 35S promoter.

11. A cell line which is transformed by the vector of claim 7.

12. A host plant transfected by the vector of claim 7.

13. The host plant of claim 12, wherein the host plant is Cucurbitaceae plant.

14. A composition for transforming a plant, comprising the Cucumber fruit mottle mosaic virus (CFMMV) vector of claim 7.

15. The composition of claim 14, wherein the composition further comprises a P19 suppressor.

16. A method of inducing gene silencing or gene expression in a plant, comprising inoculating the plant with the Cucumber fruit mottle mosaic virus (CFMMV) vector of claim 7.

17. The method of claim 16, wherein the method comprises further inoculating the plant with a P19 suppressor.

18. A host plant transfected by the cell of claim 11.

19. A composition for transforming a plant, comprising the cell of claim 11.

20. A method of inducing gene silencing or gene expression in a plant, comprising inoculating the plant with the cell of claim 11.

* * * * *

UNITED STATES PATENT AND TRADEMARK OFFICE
CERTIFICATE OF CORRECTION

PATENT NO. : 10,174,332 B2
APPLICATION NO. : 15/303174
DATED : January 8, 2019
INVENTOR(S) : Gung Pyo Lee et al.

It is certified that error appears in the above-identified patent and that said Letters Patent is hereby corrected as shown below:

In the Drawings

Replace Drawing Sheet 1 of 14 with the attached Drawing Sheet 1 of 14

Replace Drawing Sheet 12 of 14 with the attached Drawing Sheet 12 of 14

In the Specification

Columns 25-26, after the last listing in sequence, Sequence 6, please insert the following:
```
<210> 7
<211> 226
<212> RNA
<213> Artificial Sequence <220>
<223> chemically synthesized <400> 7
gacauagacg ucggucagcc cuaaaaugcc auuuaacua aggcuuaaua auacacugac    60
gacgacuacg gaggagguuu gggaccagaa acaaacaauc cuaaagacca caauccuagu    120
uucuaccaaa aagaggcaau ugagaccucu aacggagaaa ccaccgaugg ugguuaagau    180
aaaauuucuu cccagauucu caaucacacu agcucaggca ccaucc                    226
```

Signed and Sealed this
Twenty-sixth Day of November, 2019

Andrei Iancu
*Director of the United States Patent and Trademark Office*

```
<210> 8
<211> 21
<212> DNA
<213> Artificial Sequence

<220>
<223> chemically synthesized

<400> 8
ggaggaggga acaacaagag g                    21

<210> 9
<211> 18
<212> DNA
<213> Artificial Sequence

<220>
<223> chemically synthesized

<400> 9
agatgccgtc agtgccga                        18

<210> 10
<211> 21
<212> DNA
<213> Artificial Sequence

<220>
<223> chemically synthesized

<400> 10
cgctttgatt ttcctgaagc a                    21

<210> 11
<211> 20
<212> DNA
<213> Artificial Sequence

<220>
<223> chemically synthesized

<400> 11
gctggcaaga gtccaatagc                      20
```

<210> 12
<211> 20
<212> DNA
<213> Artificial Sequence

<220>
<223> chemically synthesized

<400> 12
ggcggatgtt gctttaaggt        20

<210> 13
<211> 19
<212> DNA
<213> Artificial Sequence

<220>
<223> chemically synthesized

<400> 13
gtggtgccct tccgtcaat         19

<210> 14
<211> 20
<212> DNA
<213> Artificial Sequence

<220>
<223> chemically synthesized

<400> 14
tgcattttga ttgccttgaa        20

<210> 15
<211> 20
<212> DNA
<213> Artificial Sequence

<220>
<223> chemically synthesized

<400> 15
tatgctcgac aattggctca        20

```
<210> 16
<211> 21
<212> DNA
<213> Artificial Sequence

<220>
<223> chemically synthesized

<400> 16
agaacggcat caaggtgaac t                    21

<210> 17
<211> 20
<212> DNA
<213> Artificial Sequence

<220>
<223> chemically synthesized

<400> 17
tgctcaggta gtggttgtcg                      20   --
```

(SEQ ID NO:7)

FIG. 11

| Primer | Sequence | | |
|--------|----------|---|---|
| SJ 413 | 5'- GGAGGAGGGAACAACAAGAGG-3' | (SEQ ID NO:8) | Nb-GADPH-F |
| SJ 314 | 5'- AGATGCCGTCAGTGCCGA-3' | (SEQ ID NO:9) | Nb-GADPH-R |
| SJ 565 | 5'-CGCTTTGATTTTCCTGAAGCA-3' | (SEQ ID NO:10) | NbPDS-F |
| SJ 566 | 5'- GCTGGCAAGAGTCCAATAGC-3' | (SEQ ID NO:11) | NbPDS-R |
| SJ 415 | 5'- GGCGGATGTTGCTTTAAGGA-3' | (SEQ ID NO:12) | Cm-18S-F |
| SJ 416 | 5'-GTGGTGCCCTTCCGTCAAT-3' | (SEQ ID NO:13) | Cm-18S-R |
| SJ 561 | 5'-TGCATTTTGATTGCCTTGAA-3 | (SEQ ID NO:14) | CmPDS-F |
| SJ 562 | 5'- TATGCTCGACAATTGGCTCA-3' | (SEQ ID NO:15) | CmPDS-R |
| SJ 571 | 5'- AGAACGGCATCAAGGTGAACT-3' | (SEQ ID NO:16) | EGFP-F |
| SJ 572 | 5'- TGCTCAGGTAGTGGTTGTCG-3' | (SEQ ID NO:17) | EGFP-R |